United States Patent
Elbaz et al.

(10) Patent No.: US 6,835,539 B1
(45) Date of Patent: Dec. 28, 2004

(54) NUCLEIC SEQUENCES CODING FOR AN AT2 INTERACTING PROTEINS INTERACTING WITH THE AT2 RECEPTOR AND THEIR APPLICATIONS

(76) Inventors: Nathalie Elbaz, 7, Passage des Italiens 93170, Bagnolet (FR); Clara Nahmias, 4, Rue Bally 75003, Paris (FR); Arthur Donny Strosberg, 66, Rue de Javel 75015, Paris (FR)

( * ) Notice: Subject to any disclaimer, the term of this patent is extended or adjusted under 35 U.S.C. 154(b) by 0 days.

(21) Appl. No.: 09/762,194
(22) PCT Filed: Aug. 2, 1999
(86) PCT No.: PCT/FR99/01908
§ 371 (c)(1),
(2), (4) Date: Oct. 8, 2001
(87) PCT Pub. No.: WO00/08148
PCT Pub. Date: Feb. 17, 2000

(30) Foreign Application Priority Data

Aug. 4, 1998 (FR) .......................... 98 09997

(51) Int. Cl.$^7$ .............................. C12Q 1/68; C12N 1/21
(52) U.S. Cl. .................. 435/6; 435/252.33; 435/254.2; 435/320.1; 435/358; 536/23.5
(58) Field of Search ........................ 435/252.33, 254.2, 435/320.1, 358, 6; 536/23.5

(56) References Cited

U.S. PATENT DOCUMENTS 5,925,523 A * 7/1999 Dove et al. .................. 435/6

OTHER PUBLICATIONS

Brent et al., A Euraryotic Transcriptional Activator Bearing the DNA Specificity of a Prokaryotic Repressor, Cell, vol. 43, pp 729–736, Dec. 1985 (Part 2).*
Ma et al., Converting a Eukaryotic Transcriptional Inhibitor into an Activator, Cell, vol. 55, pp 443–446, Nov. 4, 1988.*
Fields et al., Nature, vol. 340, pp 245–246, Jul. 20, 1989.*
Bonaldo et al., Normalization and subtraction: two approaches to facilitate gene discovery, Genome Res., vol. 6, Issue 9, pp 791–806, 1996.*
Marra et al., The WashU–HHMI Mouse EST Project, GenBankEST Database, Mar. 26, 1998, accession No. AA880300.*
AF121259. Submitted Jan. 18, 1999 to Medizinische Klinik I, Klinikum Merheim, Osterheimer, Str. 200, Cologne 51109, Germany.*
Database EMEST4 Online!; EMBL; Heidelberg, Germany; AC AA880030; Mar. 30, 1998; Marra M. et al.; *Mus musculus cDNA clone 1277601*; XP002100073.
Database EMEST2 Online!EMBL., Heidelberg, Germany; AC/ID AA651757, Nov. 8, 1997, NCI–CGAP: *Homo sapiens cDNA clone IMAGE: 1188695*; XP002126887.
Bedecs et al.; *Angioiensin II type 2 receptors mediate inhibition of mitogen–activated protein kinase cascade and functional activation of SHP—1 tyrosine phosphatase*, Biochemical Journal; vol. 352, No. 2; Jul. 15, 1997, pp. 449–454; XP002094565.
Nahmias C et al.; *The angiotensin A72 receptor: searching for signal–transduction pathways and physiological function*, Trends in Pharmacological Sciences; Jul. 1995; 16 (7) 223–225; Ref. 28 Journal Code: WFT ISSN: 0165–6147; XP002100074.
Triode et al.; *A conditionally expressed third partner stabilizes or prevents the formation of a transcriptional activator in a three–hybrid system*; Journal of Biological Chemistry; vol. 37, No. 272; 1997 pp. 22995–22999; XP002051283.
Database R61U002 Online! EMBL, Heidelberg, Germany, AC AL096842; Jul. 14, 1999, Wambutt R. et al.; *Homo sapiens mRNA, cDNA DKFZp586D1519*; XP002126888.

* cited by examiner

Primary Examiner—Robert A. Wax
(74) Attorney, Agent, or Firm—Alston & Bird LLP

(57) ABSTRACT

The invention concerns nucleic sequences coding for a protein capable of interacting with the AT2 receptor, oligonucleotides included in said sequences, their applications as probes and for expressing said proteins, vectors useful for said expression, host cells containing said vectors, and study model of AT2 receptor. The invention also concerns said proteins and their uses. Said isolated nucleic acid fragment coding for a protein capable of binding with the AT2 receptor is selected among the group consisting of the sequences SEQ ID NO: 1, 3, 5, 7 and 9.

11 Claims, 14 Drawing Sheets

| LOCUS | AT2 receptor C-terminal end | 160 BP DS-DNA |
|---|---|---|

ORGANISM  Mouse
BASES     41 A    33 C    36 G    50 T

Nucleic acids  1   TGTGTTAATC CCTTCCTGTA TTGTTTTGTT GGAAACCGCT
                   TCCAACAGAA CGTCCGCAGT GTGTTTAGAG TTCCCATTAC
                   TTGGCTCCAA GGCAAGAGAG AGACTATGTC TTGCAGAAAA
              121  GGCAGTTCTC TTAGAGAAAT GGACACCTTT GTGTCTTAAA Translation into amino acids

CVNPFLYCFV GNRFQQNVRS VFRVPITWLQ GKRETMSCRK
GSSLREMDTFVS·

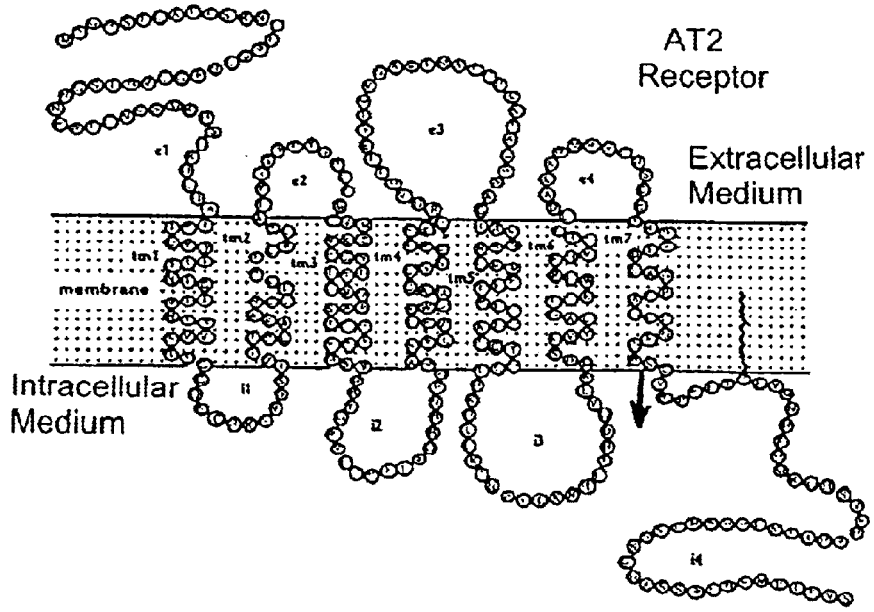

Figure 1

```
GCTACCCCCCCCCCACGCACCCCCCAATCTGGGTGGCCTGGCATTAGCATGTAAGCTTGTTTTTCTCTGGC   71

TGTATCTCTTGGCCTGGAAGAACCCCGAGTTGCCAAGAGACACAGTATGTGATGGTCCCTGGAAAAGCTGCT  143

M   L   L   S   P   K   F   S   L     9
TCCCCTGCGAAGTTCTCCCACTGGCTTCGAAGAC ATG CTG TTG TCT CCC AAA TTC TCC TTA   204

S   T   I   H   V   R   L   T   A   K   G   L   L   R   N   L   R   L    27
 TCC ACC ATC CAC GTC CGC CTA ACC GCC AAA GGA CTG CTT CGA AAC CTC CGG CTT  258

P   S   G   L   R   K   N   T   V   I   F   H   T   V   E   K   G   R    45
 CCT TCG GGG CTC AGG AAA AAC ACT GTC ATT TTC CAC ACA GTT GAA AAG GGC AGG  312

Q   K   N   P   R   S   L   C   I   Q   T   Q   T   A   P   D   V   L    63
 CAG AAG AAT CCC AGG AGC CTG TGC ATC CAG ACC CAG ACA GCT CCA GAT GTG CTG  366

S   S   E   R   T   L   E   L   A   Q   Y   K   T   K   C   E   S   Q    81
 TCC TCC GAG AGA ACG CTT GAG TTG GCC CAA TAC AAG ACA AAA TGT GAA AGC CAA  420

S   G   F   I   L   H   L   R   Q   L   L   S   R   G   N   N   K   F    99
 AGT GGA TTC ATC CTG CAC CTC AGG CAG CTT CTT TCC CGT GGT AAC AAC AAG TTT  474

E   A   L   T   V   V   I   Q   H   L   L   S   E   R   E   E   A   L   117
 GAA GCG CTG ACA GTT GTG ATC CAG CAC CTC CTG TCT GAG CGG GAG GAA GCA CTG  528

K   Q   H   K   T   L   S   Q   E   L   V   S   L   R   G   E   L   V   135
 AAG CAA CAC AAA ACC CTC TCT CAA GAA CTT GTC AGC CTC CGG GGA GAG CTA GTT  582

A   A   S   S   A   C   E   K   L   E   K   A   R   A   D   L   Q   T   153
 GCT GCT TCA AGC GCC TGT GAG AAG CTA GAA AAG GCT AGG GCT GAC TTA CAG ACA  636

A   Y   Q   E   F   V   Q   K   L   N   Q   Q   H   Q   T   D   R   T   171
 GCG TAT CAA GAA TTT GTC CAG AAA CTA AAC CAG CAG CAT CAG ACA GAC CGG ACG  690

E   L   E   N   R   L   K   D   L   Y   T   A   E   C   E   K   L   Q   189
 GAA CTG GAG AAC CGG CTG AAG GAC TTA TAC ACC GCA GAG TGT GAG AAG CTT CAG  744

S   I   Y   I   E   E   A   E   K   Y   K   T   Q   L   Q   E   Q   F   207
 AGC ATT TAC ATT GAG GAG GCA GAA AAA TAT AAA ACT CAA CTG CAA GAG CAG TTT  798

D   N   L   N   A   A   H   E   T   T   K   L   E   I   E   A   S   H   225
 GAC AAC TTA AAC GCC GCC CAT GAG ACC ACT AAG CTT GAG ATT GAA GCT AGC CAC  852

S   E   K   V   E   L   L   K   K   T   Y   E   T   S   L   S   E   I   243
 TCG GAG AAG GTG GAA TTG CTG AAG AAG ACC TAT GAA ACC TCC CTT TCA GAA ATC  906

K   K   S   H   E   M   E   K   K   S   L   E   D   L   L   N   E   K   261
 AAG AAG AGC CAT GAG ATG GAG AAG AAG TCA CTG GAG GAT CTG CTT AAT GAG AAG  960

Q   E   S   L   E   K   Q   I   N   D   L   K   S   E   N   D   A   L   279
 CAG GAA TCG CTG GAG AAA CAA ATC AAT GAT CTG AAG AGT GAA AAC GAT GCT TTA 1014

N   E   R   L   K   S   E   E   Q   K   Q   L   S   R   E   K   A   N   297
 AAC GAA AGG TTG AAA TCA GAG GAG CAA AAG CAA CTG TCA AGA GAG AAG GCG AAT 1068

S   K   N   P   Q   V   M   Y   L   E   Q   E   L   E   S   L   K   A   315
 TCC AAA AAC CCT CAG GTC ATG TAT CTG GAG CAA GAA CTA GAA AGC CTG AAG GCT 1122
```

Figure 3.1

|   |   |   |   |   |   |   |   |   |   |   |   |   |   |   |   |   |     |
|---|---|---|---|---|---|---|---|---|---|---|---|---|---|---|---|---|-----|
| V | L | E | I | K | N | E | K | L | H | Q | Q | D | M | K | L | M | K | 333 |

GTG TTA GAG ATC AAG AAT GAG AAG CTG CAC CAG CAG GAC ATG AAG CTA ATG AAG 1176

M E K L V D N N T A L V D K L K R F 351
ATG GAA AAG CTG GTG GAC AAT AAC ACA GCA TTG GTT GAC AAG CTG AAG CGA TTC 1230

Q Q E N E E L K A R M D K H M A I S 369
CAG CAG GAA AAC GAG GAG TTA AAA GCT CGC ATG GAC AAA CAC ATG GCA ATT TCA 1284

R Q L S T E Q A A L Q E S L E K E S 387
AGG CAA CTT TCC ACC GAG CAG GCC GCG CTG CAA GAG TCC CTT GAG AAG GAG TCA 1338

K V N K R L S M E N E L L W K L H 405
AAG GTC AAC AAG AGA CTG TCC ATG GAG AAC GAG GAA CTT CTG TGG AAA CTG CAC 1392

N G D L C S P K R S P T S S A I P F 423
AAC GGA GAC CTG TGC AGC CCC AAG AGA TCC CCC ACC TCC TCG GCC ATC CCT TTC 1446

Q S P R N S G S F S S P S I S P R * 440
CAG TCC CCC AGG AAT TCT GGT TCC TTC TCC AGC CCC AGC ATC TCA CCC AGA TGA 1500

CGGCTTCTGAACGCAGGAGACTCTCTGAAGGCACTGAGGTGCGCTTCTGCAGGACTGACCCTCTCATGGA 1571

ACTCGAGTTGCTGCGTTAGCTCTCTGGAATATCCCCAGGATATCGGGAGAGCAGCCGCCAACCGTATCAGC 1642

TACGTACGAATAGAGAGCTCCAATAGAAGACTTTTAACTTGGTCCAAAAGCCTCCTCCAAAAACAGATTTC 1713

GGAACTGAAGTGGACATAGTTGCACAAAGCACTTACGGAACGAGGGAACCTTGTTCTTTGCCTTCCTTCAC 1784

CTAAGCATAGGCTTTCCAG 1803

Figure 3.2

```
cagtgtgatgtggttcagaggcagcttctagacctgcaggagggagattgtattcagaggaagagcatcatt      72 ttggcaacatctgaaagtgaaaacggaagccagaaacacttggccagccctgggggatttttttcttctatg     144 cctctgtggtggaatgacatttgctgtgtaggcatctttcctctgactgtatttcttggccttgaagagtac     216 tgagtttaaaaagacagtatgtgacagtccatggaaattgcctcttctgtgaaatctcgccacctgctccga     288
```

| agac | ATG | TTG | TTG | TCT | CCC | AAA | TTC | TCC | TTA | TCC | ACC | ATT | CAC | ATA | CGA | CTG | ACG | 343 |
|------|-----|-----|-----|-----|-----|-----|-----|-----|-----|-----|-----|-----|-----|-----|-----|-----|-----|-----|
|      | M   | L   | L   | S   | P   | K   | F   | S   | L   | S   | T   | I   | H   | I   | R   | L   | T   | 17  |

| GCC | AAA | GGA | TTG | CTT | CGA | AAC | CTT | CGA | CTT | CCT | TCA | GGG | TTT | AGG | AGA | AGC | ACT | 397 |
|-----|-----|-----|-----|-----|-----|-----|-----|-----|-----|-----|-----|-----|-----|-----|-----|-----|-----|-----|
| A   | K   | G   | L   | L   | R   | N   | L   | R   | L   | P   | S   | G   | F   | R   | R   | S   | T   | 35  |

| GTT | GTT | TTC | CAC | ACA | GTT | GAA | AAG | AGC | AGG | CAA | AAG | AAT | CCT | CGA | AGC | TTA | TGT | 451 |
|-----|-----|-----|-----|-----|-----|-----|-----|-----|-----|-----|-----|-----|-----|-----|-----|-----|-----|-----|
| V   | V   | F   | H   | T   | V   | E   | K   | S   | R   | Q   | K   | N   | P   | R   | S   | L   | C   | 53  |

| ATC | CAG | CCA | CAG | ACA | GCT | CCC | GAT | GCG | CTG | CCC | CCT | GAG | AAA | ACA | CTT | GAA | TTG | 505 |
|-----|-----|-----|-----|-----|-----|-----|-----|-----|-----|-----|-----|-----|-----|-----|-----|-----|-----|-----|
| I   | Q   | P   | Q   | T   | A   | P   | D   | A   | L   | P   | P   | E   | K   | T   | L   | E   | L   | 71  |

| ACG | CAA | TAT | AAA | ACA | AAA | TGT | GAA | AAC | CAA | AGT | GGA | TTT | ATC | CTG | CAG | CTC | AAG | 559 |
|-----|-----|-----|-----|-----|-----|-----|-----|-----|-----|-----|-----|-----|-----|-----|-----|-----|-----|-----|
| T   | Q   | Y   | K   | T   | K   | C   | E   | N   | Q   | S   | G   | F   | I   | L   | Q   | L   | K   | 89  |

| CAG | CTT | CTT | GCC | TGT | GGT | AAT | ACC | AAG | TTT | GAG | GCA | TTG | ACA | GTT | GTG | ATT | CAG | 613 |
|-----|-----|-----|-----|-----|-----|-----|-----|-----|-----|-----|-----|-----|-----|-----|-----|-----|-----|-----|
| Q   | L   | L   | A   | C   | G   | N   | T   | K   | F   | E   | A   | L   | T   | V   | V   | I   | Q   | 107 |

| CAC | CTG | CTG | TCT | GAG | CGG | GAG | GAA | GCA | CTG | AAA | CAA | CAC | AAA | ACC | CTA | TCT | CAA | 667 |
|-----|-----|-----|-----|-----|-----|-----|-----|-----|-----|-----|-----|-----|-----|-----|-----|-----|-----|-----|
| H   | L   | L   | S   | E   | R   | E   | E   | A   | L   | K   | Q   | H   | K   | T   | L   | S   | Q   | 125 |

| GAA | CTT | GTT | AAC | CTC | CGG | GGA | GAG | CTA | GTC | ACT | GCT | TCA | ACC | ACC | TGT | GAG | AAA | 721 |
|-----|-----|-----|-----|-----|-----|-----|-----|-----|-----|-----|-----|-----|-----|-----|-----|-----|-----|-----|
| E   | L   | V   | N   | L   | R   | G   | E   | L   | V   | T   | A   | S   | T   | T   | C   | E   | K   | 143 |

| TTA | GAA | AAA | GCC | AGG | AAT | GAG | TTA | CAA | ACA | GTG | TAT | GAA | GCA | TTC | GTC | CAG | CAG | 775 |
|-----|-----|-----|-----|-----|-----|-----|-----|-----|-----|-----|-----|-----|-----|-----|-----|-----|-----|-----|
| L   | E   | K   | A   | R   | N   | E   | L   | Q   | T   | V   | Y   | E   | A   | F   | V   | Q   | Q   | 161 |

| CAC | CAG | GCT | GAA | AAA | ACA | GAA | CGA | GAG | AAT | CGG | CTT | AAA | GAG | TTT | TAC | ACC | AGG | 829 |
|-----|-----|-----|-----|-----|-----|-----|-----|-----|-----|-----|-----|-----|-----|-----|-----|-----|-----|-----|
| H   | Q   | A   | E   | K   | T   | E   | R   | E   | N   | R   | L   | K   | E   | F   | Y   | T   | R   | 179 |

| GAG | TAT | GAA | AAG | CTT | CGG | GAC | ACT | TAC | ATT | GAA | GAA | GCA | GAG | AAG | TAC | AAA | ATG | 883 |
|-----|-----|-----|-----|-----|-----|-----|-----|-----|-----|-----|-----|-----|-----|-----|-----|-----|-----|-----|
| E   | Y   | E   | K   | L   | R   | D   | T   | Y   | I   | E   | E   | A   | E   | K   | Y   | K   | M   | 197 |

| CAA | TTG | CAA | GAG | CAG | TTT | GAC | AAC | TTA | AAT | GCG | CAT | GAA | ACC | TCT | AAG | TTG | GAA | 937 |
|-----|-----|-----|-----|-----|-----|-----|-----|-----|-----|-----|-----|-----|-----|-----|-----|-----|-----|-----|
| Q   | L   | Q   | E   | Q   | F   | D   | N   | L   | N   | A   | H   | E   | T   | S   | K   | L   | E   | 215 |

| ATT | GAA | GCT | AGC | CAC | TCA | GAG | AAA | CTT | GAA | TTG | CTA | AAG | AAG | GCC | TAT | GAA | GCC | 991 |
|-----|-----|-----|-----|-----|-----|-----|-----|-----|-----|-----|-----|-----|-----|-----|-----|-----|-----|-----|
| I   | E   | A   | S   | H   | S   | E   | K   | L   | E   | L   | L   | K   | K   | A   | Y   | E   | A   | 233 |

| TCC | CTT | TCA | GAA | ATT | AAG | AAA | GGC | CAT | GAA | ATA | GAA | AAG | AAA | TCG | CTT | GAA | GAT | 1045 |
|-----|-----|-----|-----|-----|-----|-----|-----|-----|-----|-----|-----|-----|-----|-----|-----|-----|-----|------|
| S   | L   | S   | E   | I   | K   | K   | G   | H   | E   | I   | E   | K   | K   | S   | L   | E   | D   | 251  |

| TTA | CTT | TCT | GAG | AAG | CAG | GAA | TCG | CTA | GAG | AAG | CAA | ATC | AAT | GAT | CTG | AAG | AGT | 1099 |
|-----|-----|-----|-----|-----|-----|-----|-----|-----|-----|-----|-----|-----|-----|-----|-----|-----|-----|------|
| L   | L   | S   | E   | K   | Q   | E   | S   | L   | E   | K   | Q   | I   | N   | D   | L   | K   | S   | 269  |

| GAA | AAT | GAT | GCT | TTA | AAT | GAA | AAA | TTG | AAA | TCA | GAA | GAA | CAA | AAA | AGA | AGA | GCA | 1153 |
|-----|-----|-----|-----|-----|-----|-----|-----|-----|-----|-----|-----|-----|-----|-----|-----|-----|-----|------|
| E   | N   | D   | A   | L   | N   | E   | K   | L   | K   | S   | E   | E   | Q   | K   | R   | R   | A   | 287  |

| AGA | GAA | AAA | GCA | AAT | TTG | AAA | AAT | CCT | CAG | ATC | ATG | TAT | CTA | GAA | CAG | GAG | TTA | 1207 |
|-----|-----|-----|-----|-----|-----|-----|-----|-----|-----|-----|-----|-----|-----|-----|-----|-----|-----|------|
| R   | E   | K   | A   | N   | L   | K   | N   | P   | Q   | I   | M   | Y   | L   | E   | Q   | E   | L   | 305  |

Figure 4.1

```
GAA AGC CTG AAA GCT GTG TTA GAG ATC AAG AAT GAG AAA CTG CAT CAA CAG GAC  1261
 E   S   L   K   A   V   L   E   I   K   N   E   K   L   H   Q   Q   D   323

ATC AAG TTA ATG AAA ATG GAG AAA CTG GTG GAC AAC AAC ACA GCA TTG GTT GAC  1315
 I   K   L   M   K   M   E   K   L   V   D   N   N   T   A   L   V   D   341

AAA TTG AAG CGT TTC CAG CAG GAG AAT GAA GAA TTG AAA GCT CGG ATG GAC AAG  1369
 K   L   K   R   F   Q   Q   E   N   E   E   L   K   A   R   M   D   K   359

CAC ATG GCA ATC TCA AGG CAG CTT TCC ACG GAG CAG GCT GTT CTG CAA GAG TCG  1423
 H   M   A   I   S   R   Q   L   S   T   E   Q   A   V   L   Q   E   S   377

CTG GAG AAG GAG TCG AAA GTC AAC AAG CGA CTC TCT ATG GAA AAC GAG GAG CTT  1477
 L   E   K   E   S   K   V   N   K   R   L   S   M   E   N   E   E   L   395

CTG TGG AAA CTG CAC AAT GGG GAC CTG TGT AGC CCC AAG AGA TCC CCC ACA TCC  1531
 L   W   K   L   H   N   G   D   L   C   S   P   K   R   S   P   T   S   413

TCC GCC ATC CCT TTG CAG TCA CCA AGG AAT TCG GGC TCC TTC CCT AGC CCC AGC  1585
 S   A   I   P   L   Q   S   P   R   N   S   G   S   F   P   S   P   S   431

ATT TCA CCC AGA TGA cacgtcccaaagtccacagactctctgaaagcattttgatgcaggtctgc  1651
 I   S   P   R   *                                                        436 aggactgaccccaaggaggaacgtgggcacaagaggtatatcagcacacgtgtgatcaccgtaggtaactgg  1723 agcgtcaccaccggcggaatcgagcttctgagactggaagtctggaggaagacttttgcctccgtccaaaag  1795 attcctccaaaaaaagatttaaaaaaagatttcggcatcgacacggacgttgttgcacaaagcacttaaaga  1867 acgagagcatcttgttcattgccttttcacctaagcataagggaaaaactctcagggccctattaagatt  1939 tataacctttgtaatgttcttcaccacagacaccttcttgtgagttttcagtctgactgtgggggtgggggg  2011 tgtgaatgaaatggatgtcacagagtgtcatgtgtctgatgcagcctcctctgctgtgtattaaatgtcaaa  2083 atctgaatatatctggatatgtactaatcaaataataatcaatcaatcagcatatacatttcagccaaagcc  2155 atagaagaaaaagcaatagttgcttgaattatgatcatctaccaccaactctgctcagccctgtaacagggt  2227 agggagagggtataacaggaagagcttttgacttgtccctgtctatacattctctgtatcttttgggggtaac  2299 ttcttggcagttttcagtgttcagccatgtcagttgaaactagatttttctgtagatttttacttaccca  2371 tgtgagcctaacactatcctgtaattcatttctcaggctatgtgtaaatgtagaaccctaattttttctata  2443 aaaaaacaaactaactaactgtgtaaagaaagaaaaagggaagtaccaatgggttttccaccttattttta  2515 cctttgatctaccccttgcagatttaacctgtcttcttccctccattattctcatttttccttttaccttct  2587 ccaccatccagagccacaaaagcaaaccttctacctcctacctactttctctgggacaaggataaaggaat  2659 atgattttccagagccccagagccagctcatcttccaggtgctgaaaccactttccaaataaactaaagcct  2731 ggatttgatattacaaattttgggaaatcttagaataaagaacgagaacaaggaagtcattggctagtataa  2803 ttaagaaaggtaggattcagtgcttaccgatgatgcagtacttgatagaagaaaacagtctgggaggatagc  2875 gctcatttttcagttacccctttaaggagtccctttgtctttgggaaagtagcagaatggtccgcttctttcc  2947 catgagtggaaaatgtggcttgtccaactctcctccaggttgcatttcagtttcttttccaaaacttattacc  3019
```

Figure 4.2

```
tccctaatcctgagactttggaaaaggtggaaggaagaactgttgctttatctcccctccctgcatgtgt  3091
caacattgtgatgtcagtatttactaatctacattcagtggctgtacaaataacagctgtagtaagaaga  3163
ttcaggatgctagaggtgaatatttgggtcatttacatgtacactacatagcaagttgatactcatgttgca  3235
tgttcttttaaattagtgattttgtgtcttaagtctttaacttccaatacttcatcatgtatgtaaccttcc  3307
atgtttgcttctgataaatggaaatgtaggttcactgccacttcatgagatatctctgctcacgcttccaag  3379
ttgttctcaatgacattagccaaagttgggtttgccattcatccctaggcatggtaaatcttgtgttgttc  3451
cctgctgtcctccgtattacgtgaccggcaaataaatctcatagcagttaatataaaacatctttggaggat  3523
gggagagaacaggagggaagatgggaaacaaaatagagaattcttaagattttgtttaaaccaaatgtttca  3595
tgtagaatgcaaaatgttggcacgtcaaaaatatgaatgtgtagacaactgtagttgtgctcagtttgtagt  3667
gatgggaagtgtattttactctgatcaaataaataatgctggaatactcaaaaaaaaaaaaaaaaaaaaaa  3739
aaa                                                                      3742
```

Figure 4.3

```
                            6 histidines
                    ┌─────────────────────────────┐
 98.. ATG CGG GGT TCT CAT CAT CAT CAT CAT CAT GGT ATG
134   GCT AGC ATG ACT GGT GGA CAG CAA ATG GGT CGG GAT
170   CTG TAC GAC GAT GAC GAT AAG GAT CGA TGG GGA TCC
                                                 ─────
                                                 BamH I
206   GAG CTC GAG ATC TGC AGC TGG TAC CAT GGA ATT CGA
242   AGC TTG ATC CGG CTG CTA ACA AAG CCC GAA AGG AAG
278   CTG AGT TGG CTG CCA CCG CTG AGC AAT AAC TAG...
```

*Figure 6*

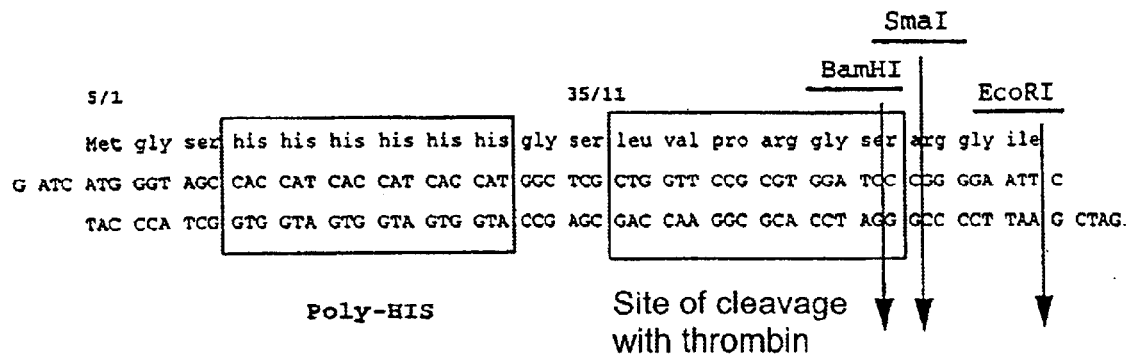
PolyHIS insertion into pBackpack in BamHI
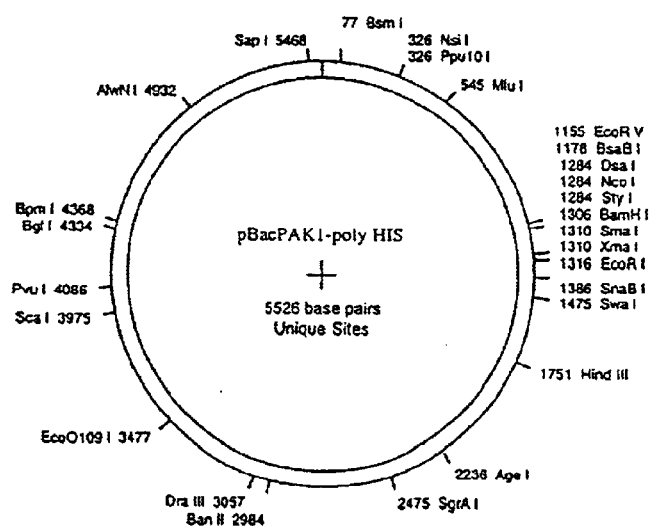
Figure 8

CHO-hAT2
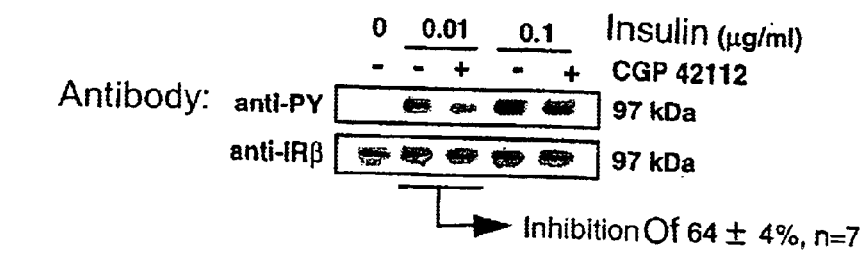
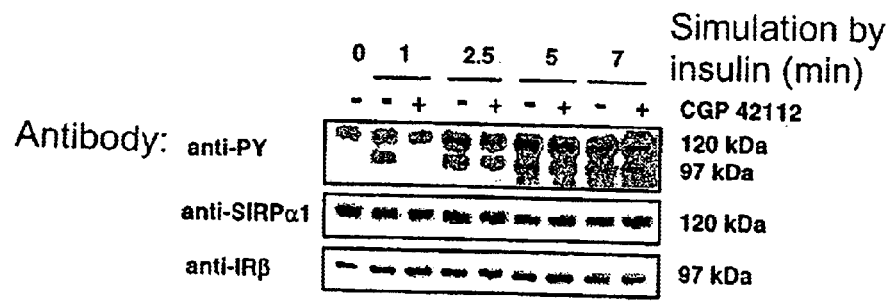
CHO-hAT2 et CHO-hAT2-ATIP
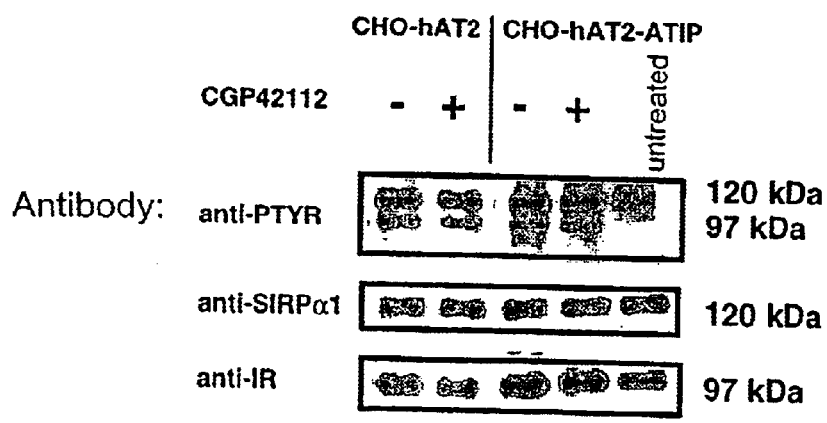
Figure 11

SEQUENCE LISTING

<160> NUMBER OF SEQ ID NOS: 12

<210> SEQ ID NO 1
<211> LENGTH: 1803
<212> TYPE: DNA
<213> ORGANISM: Mus musculus
<220> FEATURE:
<221> NAME/KEY: CDS
<222> LOCATION: (178)...(1500)

<400> SEQUENCE: 1

```
gctaccccc  ccccacgcac  cccccaatct  gggtggcctg  gcattagcat  gtaagcttgt      60
ttttctctgg  ctgtatctct  tggcctggaa  gaaccccgag  ttgccaagag  acacagtatg     120
tgatggtccc  tggaaaagct  gcttcccctg  cgaagttctc  ccactggctt  cgaagac atg    180
                                                                    Met
                                                                     1 ctg ttg tct ccc aaa ttc tcc tta tcc acc atc cac gtc cgc cta acc              228
Leu Leu Ser Pro Lys Phe Ser Leu Ser Thr Ile His Val Arg Leu Thr
          5                  10                  15 gcc aaa gga ctg ctt cga aac ctc cgg ctt cct tcg ggg ctc agg aaa              276
Ala Lys Gly Leu Leu Arg Asn Leu Arg Leu Pro Ser Gly Leu Arg Lys
         20                  25                  30 aac act gtc att ttc cac aca gtt gaa aag ggc agg cag aag aat ccc              324
Asn Thr Val Ile Phe His Thr Val Glu Lys Gly Arg Gln Lys Asn Pro
```

-continued

```
            35                  40                  45
agg agc ctg tgc atc cag acc cag aca gct cca gat gtg ctg tcc tcc     372
Arg Ser Leu Cys Ile Gln Thr Gln Thr Ala Pro Asp Val Leu Ser Ser
 50                  55                  60                  65 gag aga acg ctt gag ttg gcc caa tac aag aca aaa tgt gaa agc caa     420
Glu Arg Thr Leu Glu Leu Ala Gln Tyr Lys Thr Lys Cys Glu Ser Gln
                 70                  75                  80 agt gga ttc atc ctg cac ctc agg cag ctt ctt tcc cgt ggt aac aac     468
Ser Gly Phe Ile Leu His Leu Arg Gln Leu Leu Ser Arg Gly Asn Asn
             85                  90                  95 aag ttt gaa gcg ctg aca gtt gtg atc cag cac ctc ctg tct gag cgg     516
Lys Phe Glu Ala Leu Thr Val Val Ile Gln His Leu Leu Ser Glu Arg
         100                 105                 110 gag gaa gca ctg aag caa cac aaa acc ctc tct caa gaa ctt gtc agc     564
Glu Glu Ala Leu Lys Gln His Lys Thr Leu Ser Gln Glu Leu Val Ser
     115                 120                 125 ctc cgg gga gag cta gtt gct gct tca agc gcc tgt gag aag cta gaa     612
Leu Arg Gly Glu Leu Val Ala Ala Ser Ser Ala Cys Glu Lys Leu Glu
130                 135                 140                 145 aag gct agg gct gac tta cag aca gcg tat caa gaa ttt gtc cag aaa     660
Lys Ala Arg Ala Asp Leu Gln Thr Ala Tyr Gln Glu Phe Val Gln Lys
                 150                 155                 160 cta aac cag cag cat cag aca gac cgg acg gaa ctg gag aac cgg ctg     708
Leu Asn Gln Gln His Gln Thr Asp Arg Thr Glu Leu Glu Asn Arg Leu
             165                 170                 175 aag gac tta tac acc gca gag tgt gag aag ctt cag agc att tac att     756
Lys Asp Leu Tyr Thr Ala Glu Cys Glu Lys Leu Gln Ser Ile Tyr Ile
         180                 185                 190 gag gag gca gaa aaa tat aaa act caa ctg caa gag cag ttt gac aac     804
Glu Glu Ala Glu Lys Tyr Lys Thr Gln Leu Gln Glu Gln Phe Asp Asn
     195                 200                 205 tta aac gcc gcc cat gag acc act aag ctt gag att gaa gct agc cac     852
Leu Asn Ala Ala His Glu Thr Thr Lys Leu Glu Ile Glu Ala Ser His
210                 215                 220                 225 tcg gag aag gtg gaa ttg ctg aag aag acc tat gaa acc tcc ctt tca     900
Ser Glu Lys Val Glu Leu Leu Lys Lys Thr Tyr Glu Thr Ser Leu Ser
                 230                 235                 240 gaa atc aag aag agc cat gag atg gag aag aag tca ctg gag gat ctg     948
Glu Ile Lys Lys Ser His Glu Met Glu Lys Lys Ser Leu Glu Asp Leu
             245                 250                 255 ctt aat gag aag cag gaa tcg ctg gag aaa caa atc aat gat ctg aag     996
Leu Asn Glu Lys Gln Glu Ser Leu Glu Lys Gln Ile Asn Asp Leu Lys
         260                 265                 270 agt gaa aac gat gct tta aac gaa agg ttg aaa tca gag gag caa aag    1044
Ser Glu Asn Asp Ala Leu Asn Glu Arg Leu Lys Ser Glu Glu Gln Lys
     275                 280                 285 caa ctg tca aga gag aag gcg aat tcc aaa aac cct cag gtc atg tat    1092
Gln Leu Ser Arg Glu Lys Ala Asn Ser Lys Asn Pro Gln Val Met Tyr
290                 295                 300                 305 ctg gag caa gaa cta gaa agc ctg aag gct gtg tta gag atc aag aat    1140
Leu Glu Gln Glu Leu Glu Ser Leu Lys Ala Val Leu Glu Ile Lys Asn
                 310                 315                 320 gag aag ctg cac cag cag gac atg aag cta atg aag atg gaa aag ctg    1188
Glu Lys Leu His Gln Gln Asp Met Lys Leu Met Lys Met Glu Lys Leu
             325                 330                 335 gtg gac aat aac aca gca ttg gtt gac aag ctg aag cga ttc cag cag    1236
Val Asp Asn Asn Thr Ala Leu Val Asp Lys Leu Lys Arg Phe Gln Gln
         340                 345                 350 gaa aac gag gag tta aaa gct cgc atg gac aaa cac atg gca att tca    1284
```

-continued

| | | | | | | | | | | | | |
|---|---|---|---|---|---|---|---|---|---|---|---|---|
| Glu | Asn | Glu | Glu | Leu | Lys | Ala | Arg | Met | Asp | Lys | His | Met | Ala | Ile | Ser |
| | 355 | | | | 360 | | | | | 365 | | | | | |

```
agg caa ctt tcc acc gag cag gcc gcg ctg caa gag tcc ctt gag aag    1332
Arg Gln Leu Ser Thr Glu Gln Ala Ala Leu Gln Glu Ser Leu Glu Lys
370             375                 380                 385 gag tca aag gtc aac aag aga ctg tcc atg gag aac gag gaa ctt ctg    1380
Glu Ser Lys Val Asn Lys Arg Leu Ser Met Glu Asn Glu Glu Leu Leu
            390                 395                 400 tgg aaa ctg cac aac gga gac ctg tgc agc ccc aag aga tcc ccc acc    1428
Trp Lys Leu His Asn Gly Asp Leu Cys Ser Pro Lys Arg Ser Pro Thr
                405                 410                 415 tcc tcg gcc atc cct ttc cag tcc ccc agg aat tct ggt tcc ttc tcc    1476
Ser Ser Ala Ile Pro Phe Gln Ser Pro Arg Asn Ser Gly Ser Phe Ser
            420                 425                 430 agc ccc agc atc tca ccc aga tga cggcttctga acgcaggaga ctctctgaag   1530
Ser Pro Ser Ile Ser Pro Arg  *
            435             440 gcactgaggt gcgcttctgc aggactgacc ctctcatggg aactcgagtt gctgcgttag  1590
ctctctggaa tatccccagg atatcgggag agcagccgcc aaccgtatca gctacgtacg  1650
aatagagagc tccaatagaa gacttttaac ttggtccaaa agcctcctcc aaaaacagat  1710
ttcggaactg aagtggacat agttgcacaa agcacttacg gaacgaggga accttgttct  1770
ttgccttcct tcacctaagc ataggctttc cag                               1803
```

<210> SEQ ID NO 2
<211> LENGTH: 440
<212> TYPE: PRT
<213> ORGANISM: Mus musculus

<400> SEQUENCE: 2

```
Met Leu Leu Ser Pro Lys Phe Ser Leu Ser Thr Ile His Val Arg Leu
 1               5                  10                  15

Thr Ala Lys Gly Leu Leu Arg Asn Leu Arg Leu Pro Ser Gly Leu Arg
                20                  25                  30

Lys Asn Thr Val Ile Phe His Thr Val Glu Lys Gly Arg Gln Lys Asn
            35                  40                  45

Pro Arg Ser Leu Cys Ile Gln Thr Gln Thr Ala Pro Asp Val Leu Ser
        50                  55                  60

Ser Glu Arg Thr Leu Glu Leu Ala Gln Tyr Lys Thr Lys Cys Glu Ser
 65                  70                  75                  80

Gln Ser Gly Phe Ile Leu His Leu Arg Gln Leu Leu Ser Arg Gly Asn
                85                  90                  95

Asn Lys Phe Glu Ala Leu Thr Val Val Ile Gln His Leu Leu Ser Glu
                100                 105                 110

Arg Glu Glu Ala Leu Lys Gln His Lys Thr Leu Ser Gln Glu Leu Val
            115                 120                 125

Ser Leu Arg Gly Glu Leu Val Ala Ala Ser Ser Ala Cys Glu Lys Leu
        130                 135                 140

Glu Lys Ala Arg Ala Asp Leu Gln Thr Ala Tyr Gln Glu Phe Val Gln
145                 150                 155                 160

Lys Leu Asn Gln Gln His Gln Thr Asp Arg Thr Glu Leu Glu Asn Arg
                165                 170                 175

Leu Lys Asp Leu Tyr Thr Ala Glu Cys Glu Lys Leu Gln Ser Ile Tyr
                180                 185                 190

Ile Glu Glu Ala Glu Lys Tyr Lys Thr Gln Leu Gln Glu Gln Phe Asp
            195                 200                 205
```

-continued

```
Asn Leu Asn Ala Ala His Glu Thr Thr Lys Leu Glu Ile Glu Ala Ser
    210                 215                 220
His Ser Glu Lys Val Glu Leu Leu Lys Lys Thr Tyr Glu Thr Ser Leu
225                 230                 235                 240
Ser Glu Ile Lys Lys Ser His Glu Met Glu Lys Lys Ser Leu Glu Asp
                245                 250                 255
Leu Leu Asn Glu Lys Gln Glu Ser Leu Glu Lys Gln Ile Asn Asp Leu
            260                 265                 270
Lys Ser Glu Asn Asp Ala Leu Asn Glu Arg Leu Lys Ser Glu Glu Gln
        275                 280                 285
Lys Gln Leu Ser Arg Glu Lys Ala Asn Ser Lys Asn Pro Gln Val Met
    290                 295                 300
Tyr Leu Glu Gln Glu Leu Glu Ser Leu Lys Ala Val Leu Glu Ile Lys
305                 310                 315                 320
Asn Glu Lys Leu His Gln Gln Asp Met Lys Leu Met Lys Met Glu Lys
                325                 330                 335
Leu Val Asp Asn Asn Thr Ala Leu Val Asp Lys Leu Lys Arg Phe Gln
            340                 345                 350
Gln Glu Asn Glu Glu Leu Lys Ala Arg Met Asp Lys His Met Ala Ile
        355                 360                 365
Ser Arg Gln Leu Ser Thr Glu Gln Ala Ala Leu Gln Glu Ser Leu Glu
    370                 375                 380
Lys Glu Ser Lys Val Asn Lys Arg Leu Ser Met Glu Asn Glu Glu Leu
385                 390                 395                 400
Leu Trp Lys Leu His Asn Gly Asp Leu Cys Ser Pro Lys Arg Ser Pro
                405                 410                 415
Thr Ser Ser Ala Ile Pro Phe Gln Ser Pro Arg Asn Ser Gly Ser Phe
            420                 425                 430
Ser Ser Pro Ser Ile Ser Pro Arg
        435                 440

<210> SEQ ID NO 3
<211> LENGTH: 1323
<212> TYPE: DNA
<213> ORGANISM: Mus musculus
<220> FEATURE:
<221> NAME/KEY: CDS
<222> LOCATION: (1)...(1323)

<400> SEQUENCE: 3 atg ctg ttg tct ccc aaa ttc tcc tta tcc acc atc cac gtc cgc cta      48
Met Leu Leu Ser Pro Lys Phe Ser Leu Ser Thr Ile His Val Arg Leu
1               5                   10                  15 acc gcc aaa gga ctg ctt cga aac ctc cgg ctt cct tcg ggg ctc agg      96
Thr Ala Lys Gly Leu Leu Arg Asn Leu Arg Leu Pro Ser Gly Leu Arg
                20                  25                  30 aaa aac act gtc att ttc cac aca gtt gaa aag ggc agg cag aag aat     144
Lys Asn Thr Val Ile Phe His Thr Val Glu Lys Gly Arg Gln Lys Asn
            35                  40                  45 ccc agg agc ctg tgc atc cag acc cag aca gct cca gat gtg ctg tcc     192
Pro Arg Ser Leu Cys Ile Gln Thr Gln Thr Ala Pro Asp Val Leu Ser
        50                  55                  60 tcc gag aga acg ctt gag ttg gcc caa tac aag aca aaa tgt gaa agc     240
Ser Glu Arg Thr Leu Glu Leu Ala Gln Tyr Lys Thr Lys Cys Glu Ser
65                  70                  75                  80 caa agt gga ttc atc ctg cac ctc agg cag ctt ctt tcc cgt ggt aac     288
Gln Ser Gly Phe Ile Leu His Leu Arg Gln Leu Leu Ser Arg Gly Asn
                85                  90                  95
```

-continued

|  | 85 | 90 | 95 |  |
|---|---|---|---|---|
| aac aag ttt gaa gcg ctg aca gtt gtg atc cag cac ctc ctg tct gag<br>Asn Lys Phe Glu Ala Leu Thr Val Val Ile Gln His Leu Leu Ser Glu<br>100 105 110 | | | | 336 |
| cgg gag gaa gca ctg aag caa cac aaa acc ctc tct caa gaa ctt gtc<br>Arg Glu Glu Ala Leu Lys Gln His Lys Thr Leu Ser Gln Glu Leu Val<br>115 120 125 | | | | 384 |
| agc ctc cgg gga gag cta gtt gct gct tca agc gcc tgt gag aag cta<br>Ser Leu Arg Gly Glu Leu Val Ala Ala Ser Ser Ala Cys Glu Lys Leu<br>130 135 140 | | | | 432 |
| gaa aag gct agg gct gac tta cag aca gcg tat caa gaa ttt gtc cag<br>Glu Lys Ala Arg Ala Asp Leu Gln Thr Ala Tyr Gln Glu Phe Val Gln<br>145 150 155 160 | | | | 480 |
| aaa cta aac cag cag cat cag aca gac cgg acg gaa ctg gag aac cgg<br>Lys Leu Asn Gln Gln His Gln Thr Asp Arg Thr Glu Leu Glu Asn Arg<br>165 170 175 | | | | 528 |
| ctg aag gac tta tac acc gca gag tgt gag aag ctt cag agc att tac<br>Leu Lys Asp Leu Tyr Thr Ala Glu Cys Glu Lys Leu Gln Ser Ile Tyr<br>180 185 190 | | | | 576 |
| att gag gag gca gaa aaa tat aaa act caa ctg caa gag cag ttt gac<br>Ile Glu Glu Ala Glu Lys Tyr Lys Thr Gln Leu Gln Glu Gln Phe Asp<br>195 200 205 | | | | 624 |
| aac tta aac gcc gcc cat gag acc act aag ctt gag att gaa gct agc<br>Asn Leu Asn Ala Ala His Glu Thr Thr Lys Leu Glu Ile Glu Ala Ser<br>210 215 220 | | | | 672 |
| cac tcg gag aag gtg gaa ttg ctg aag aag acc tat gaa acc tcc ctt<br>His Ser Glu Lys Val Glu Leu Leu Lys Lys Thr Tyr Glu Thr Ser Leu<br>225 230 235 240 | | | | 720 |
| tca gaa atc aag aag agc cat gag atg gag aag aag tca ctg gag gat<br>Ser Glu Ile Lys Lys Ser His Glu Met Glu Lys Lys Ser Leu Glu Asp<br>245 250 255 | | | | 768 |
| ctg ctt aat gag aag cag gaa tcg ctg gag aaa caa atc aat gat ctg<br>Leu Leu Asn Glu Lys Gln Glu Ser Leu Glu Lys Gln Ile Asn Asp Leu<br>260 265 270 | | | | 816 |
| aag agt gaa aac gat gct tta aac gaa agg ttg aaa tca gag gag caa<br>Lys Ser Glu Asn Asp Ala Leu Asn Glu Arg Leu Lys Ser Glu Glu Gln<br>275 280 285 | | | | 864 |
| aag caa ctg tca aga gag aag gcg aat tcc aaa aac cct cag gtc atg<br>Lys Gln Leu Ser Arg Glu Lys Ala Asn Ser Lys Asn Pro Gln Val Met<br>290 295 300 | | | | 912 |
| tat ctg gag caa gaa cta gaa agc ctg aag gct gtg tta gag atc aag<br>Tyr Leu Glu Gln Glu Leu Glu Ser Leu Lys Ala Val Leu Glu Ile Lys<br>305 310 315 320 | | | | 960 |
| aat gag aag ctg cac cag cag gac atg aag cta atg aag atg gaa aag<br>Asn Glu Lys Leu His Gln Gln Asp Met Lys Leu Met Lys Met Glu Lys<br>325 330 335 | | | | 1008 |
| ctg gtg gac aat aac aca gca ttg gtt gac aag ctg aag cga ttc cag<br>Leu Val Asp Asn Asn Thr Ala Leu Val Asp Lys Leu Lys Arg Phe Gln<br>340 345 350 | | | | 1056 |
| cag gaa aac gag gag tta aaa gct cgc atg gac aaa cac atg gca att<br>Gln Glu Asn Glu Glu Leu Lys Ala Arg Met Asp Lys His Met Ala Ile<br>355 360 365 | | | | 1104 |
| tca agg caa ctt tcc acc gag cag gcc gcg ctg caa gag tcc ctt gag<br>Ser Arg Gln Leu Ser Thr Glu Gln Ala Ala Leu Gln Glu Ser Leu Glu<br>370 375 380 | | | | 1152 |
| aag gag tca aag gtc aac aag aga ctg tcc atg gag aac gag gaa ctt<br>Lys Glu Ser Lys Val Asn Lys Arg Leu Ser Met Glu Asn Glu Glu Leu<br>385 390 395 400 | | | | 1200 |
| ctg tgg aaa ctg cac aac gga gac ctg tgc agc ccc aag aga tcc ccc | | | | 1248 |

-continued

```
Leu Trp Lys Leu His Asn Gly Asp Leu Cys Ser Pro Lys Arg Ser Pro
            405                 410                 415 acc tcc tcg gcc atc cct ttc cag tcc ccc agg aat tct ggt tcc ttc      1296
Thr Ser Ser Ala Ile Pro Phe Gln Ser Pro Arg Asn Ser Gly Ser Phe
            420                 425                 430 tcc agc ccc agc atc tca ccc aga tga                                  1323
Ser Ser Pro Ser Ile Ser Pro Arg  *
            435                 440

<210> SEQ ID NO 4
<211> LENGTH: 440
<212> TYPE: PRT
<213> ORGANISM: Mus musculus

<400> SEQUENCE: 4

Met Leu Leu Ser Pro Lys Phe Ser Leu Ser Thr Ile His Val Arg Leu
 1               5                  10                  15

Thr Ala Lys Gly Leu Leu Arg Asn Leu Arg Leu Pro Ser Gly Leu Arg
                20                  25                  30

Lys Asn Thr Val Ile Phe His Thr Val Glu Lys Gly Arg Gln Lys Asn
            35                  40                  45

Pro Arg Ser Leu Cys Ile Gln Thr Gln Thr Ala Pro Asp Val Leu Ser
    50                  55                  60

Ser Glu Arg Thr Leu Glu Leu Ala Gln Tyr Lys Thr Lys Cys Glu Ser
65                  70                  75                  80

Gln Ser Gly Phe Ile Leu His Leu Arg Gln Leu Leu Ser Arg Gly Asn
                85                  90                  95

Asn Lys Phe Glu Ala Leu Thr Val Val Ile Gln His Leu Leu Ser Glu
            100                 105                 110

Arg Glu Glu Ala Leu Lys Gln His Lys Thr Leu Ser Gln Glu Leu Val
        115                 120                 125

Ser Leu Arg Gly Glu Leu Val Ala Ala Ser Ser Ala Cys Glu Lys Leu
    130                 135                 140

Glu Lys Ala Arg Ala Asp Leu Gln Thr Ala Tyr Gln Glu Phe Val Gln
145                 150                 155                 160

Lys Leu Asn Gln Gln His Gln Thr Asp Arg Thr Glu Leu Glu Asn Arg
                165                 170                 175

Leu Lys Asp Leu Tyr Thr Ala Glu Cys Glu Lys Leu Gln Ser Ile Tyr
            180                 185                 190

Ile Glu Glu Ala Glu Lys Tyr Lys Thr Gln Leu Gln Glu Gln Phe Asp
        195                 200                 205

Asn Leu Asn Ala Ala His Glu Thr Thr Lys Leu Glu Ile Glu Ala Ser
    210                 215                 220

His Ser Glu Lys Val Glu Leu Leu Lys Lys Thr Tyr Glu Thr Ser Leu
225                 230                 235                 240

Ser Glu Ile Lys Lys Ser His Glu Met Glu Lys Ser Leu Glu Asp
                245                 250                 255

Leu Leu Asn Glu Lys Gln Glu Ser Leu Glu Lys Gln Ile Asn Asp Leu
            260                 265                 270

Lys Ser Glu Asn Asp Ala Leu Asn Glu Arg Leu Lys Ser Glu Glu Gln
        275                 280                 285

Lys Gln Leu Ser Arg Glu Lys Ala Asn Ser Lys Asn Pro Gln Val Met
    290                 295                 300

Tyr Leu Glu Gln Glu Leu Glu Ser Leu Lys Ala Val Leu Glu Ile Lys
305                 310                 315                 320
```

```
Asn Glu Lys Leu His Gln Gln Asp Met Lys Leu Met Lys Met Glu Lys
            325                 330                 335

Leu Val Asp Asn Asn Thr Ala Leu Val Asp Lys Leu Lys Arg Phe Gln
            340                 345                 350

Gln Glu Asn Glu Glu Leu Lys Ala Arg Met Asp Lys His Met Ala Ile
            355                 360                 365

Ser Arg Gln Leu Ser Thr Glu Gln Ala Ala Leu Gln Glu Ser Leu Glu
    370                 375                 380

Lys Glu Ser Lys Val Asn Lys Arg Leu Ser Met Glu Asn Glu Glu Leu
385                 390                 395                 400

Leu Trp Lys Leu His Asn Gly Asp Leu Cys Ser Pro Lys Arg Ser Pro
                    405                 410                 415

Thr Ser Ser Ala Ile Pro Phe Gln Ser Pro Arg Asn Ser Gly Ser Phe
                420                 425                 430

Ser Ser Pro Ser Ile Ser Pro Arg
        435                 440

<210> SEQ ID NO 5
<211> LENGTH: 354
<212> TYPE: DNA
<213> ORGANISM: Artificial Sequence
<220> FEATURE:
<221> NAME/KEY: CDS
<222> LOCATION: (1)...(354)
<223> OTHER INFORMATION: Insert identified by two-hybrid screening of a
      M. musculus foetal cDNA library
<223> OTHER INFORMATION: Insert identified by two-hybrid screening of a
      M. musculus foetal cDNA library

<400> SEQUENCE: 5 cat cag aca gac cgg acg gaa ctg gag aac cgg ctg aag gac tta tac     48
His Gln Thr Asp Arg Thr Glu Leu Glu Asn Arg Leu Lys Asp Leu Tyr
  1               5                  10                  15 acc gca gag tgt gag aag ctt cag agc att tac att gag gag gca gaa    96
Thr Ala Glu Cys Glu Lys Leu Gln Ser Ile Tyr Ile Glu Glu Ala Glu
             20                  25                  30 aaa tat aaa act caa ctg caa gag cag ttt gac aac tta aac gcc gcc   144
Lys Tyr Lys Thr Gln Leu Gln Glu Gln Phe Asp Asn Leu Asn Ala Ala
         35                  40                  45 cat gag acc act aag ctt gag att gag gct agc cac tcg gag aag gtg   192
His Glu Thr Thr Lys Leu Glu Ile Glu Ala Ser His Ser Glu Lys Val
     50                  55                  60 gaa ttg ctg aag aag acc tat gaa acc tcc ctt tca gaa atc aag aag   240
Glu Leu Leu Lys Lys Thr Tyr Glu Thr Ser Leu Ser Glu Ile Lys Lys
 65                  70                  75                  80 agc cat gag atg gag aag aag tca ctg gag gat ctg ctt aat gag aag   288
Ser His Glu Met Glu Lys Lys Ser Leu Glu Asp Leu Leu Asn Glu Lys
                 85                  90                  95 cag gaa tcg ctg gag aaa caa atc aat gat ctg aag agt gaa aac gat   336
Gln Glu Ser Leu Glu Lys Gln Ile Asn Asp Leu Lys Ser Glu Asn Asp
            100                 105                 110 gct tta aac gaa agg ttg                                            354
Ala Leu Asn Glu Arg Leu
        115

<210> SEQ ID NO 6
<211> LENGTH: 118
<212> TYPE: PRT
<213> ORGANISM: Artificial Sequence
<220> FEATURE:
<223> OTHER INFORMATION: Insert identified by yeast two hybrid screening
      of a M. musculus fetal cDNA library
```

-continued

```
<400> SEQUENCE: 6

His Gln Thr Asp Arg Thr Glu Leu Glu Asn Arg Leu Lys Asp Leu Tyr
  1               5                  10                  15

Thr Ala Glu Cys Glu Lys Leu Gln Ser Ile Tyr Ile Glu Glu Ala Glu
             20                  25                  30

Lys Tyr Lys Thr Gln Leu Gln Glu Gln Phe Asp Asn Leu Asn Ala Ala
         35                  40                  45

His Glu Thr Thr Lys Leu Glu Ile Glu Ala Ser His Ser Glu Lys Val
 50                  55                  60

Glu Leu Leu Lys Lys Thr Tyr Glu Thr Ser Leu Ser Glu Ile Lys Lys
 65                  70                  75                  80

Ser His Glu Met Glu Lys Lys Ser Leu Glu Asp Leu Leu Asn Glu Lys
                 85                  90                  95

Gln Glu Ser Leu Glu Lys Gln Ile Asn Asp Leu Lys Ser Glu Asn Asp
            100                 105                 110

Ala Leu Asn Glu Arg Leu
        115

<210> SEQ ID NO 7
<211> LENGTH: 3742
<212> TYPE: DNA
<213> ORGANISM: Homo sapiens
<220> FEATURE:
<221> NAME/KEY: CDS
<222> LOCATION: (293)...(1600)

<400> SEQUENCE: 7
cagtgtgatg tggttcagag gcagcttcta gacctgcagg agggagattg tattcagagg      60
aagagcatca ttttggcaac atctgaaagt gaaaacggaa gccagaaaca cttggccagc     120
cctgggggat ttttttcttc tatgcctctg tggtggaatg acatttgctg tgtaggcatc     180
tttcctctga ctgtatttct tggccttgaa gagtactgag tttaaaaaga cagtatgtga     240
cagtccatgg aaattgcctc ttctgtgaaa tctcgccacc tgctccgaag ac atg ttg    298
                                                          Met Leu
                                                            1 ttg tct ccc aaa ttc tcc tta tcc acc att cac ata cga ctg acg gcc     346
Leu Ser Pro Lys Phe Ser Leu Ser Thr Ile His Ile Arg Leu Thr Ala
        5                  10                  15 aaa gga ttg ctt cga aac ctt cga ctt cct tca ggg ttt agg aga agc     394
Lys Gly Leu Leu Arg Asn Leu Arg Leu Pro Ser Gly Phe Arg Arg Ser
     20                  25                  30 act gtt gtt ttc cac aca gtt gaa aag agc agg caa aag aat cct cga     442
Thr Val Val Phe His Thr Val Glu Lys Ser Arg Gln Lys Asn Pro Arg
 35                  40                  45                  50 agc tta tgt atc cag cca cag aca gct ccc gat gcg ctg ccc cct gag     490
Ser Leu Cys Ile Gln Pro Gln Thr Ala Pro Asp Ala Leu Pro Pro Glu
             55                  60                  65 aaa aca ctt gaa ttg acg caa tat aaa aca aaa tgt gaa aac caa agt     538
Lys Thr Leu Glu Leu Thr Gln Tyr Lys Thr Lys Cys Glu Asn Gln Ser
         70                  75                  80 gga ttt atc ctg cag ctc aag cag ctt ctt gcc tgt ggt aat acc aag     586
Gly Phe Ile Leu Gln Leu Lys Gln Leu Leu Ala Cys Gly Asn Thr Lys
     85                  90                  95 ttt gag gca ttg aca gtt gtg att cag cac ctg ctg tct gag cgg gag     634
Phe Glu Ala Leu Thr Val Val Ile Gln His Leu Leu Ser Glu Arg Glu
100                 105                 110 gaa gca ctg aaa caa cac aaa acc cta tct caa gaa ctt gtt aac ctc     682
```

-continued

| | | | | | | | | | | | | | | | |
|---|---|---|---|---|---|---|---|---|---|---|---|---|---|---|---|
| Glu | Ala | Leu | Lys | Gln | His | Lys | Thr | Leu | Ser | Gln | Glu | Leu | Val | Asn | Leu |
| 115 | | | | | 120 | | | | | 125 | | | | | 130 |

| cgg | gga | gag | cta | gtc | act | gct | tca | acc | acc | tgt | gag | aaa | tta | gaa | aaa | 730 |
|---|---|---|---|---|---|---|---|---|---|---|---|---|---|---|---|---|
| Arg | Gly | Glu | Leu | Val | Thr | Ala | Ser | Thr | Thr | Cys | Glu | Lys | Leu | Glu | Lys | |
| | | | | 135 | | | | | 140 | | | | | 145 | | |

| gcc | agg | aat | gag | tta | caa | aca | gtg | tat | gaa | gca | ttc | gtc | cag | cag | cac | 778 |
|---|---|---|---|---|---|---|---|---|---|---|---|---|---|---|---|---|
| Ala | Arg | Asn | Glu | Leu | Gln | Thr | Val | Tyr | Glu | Ala | Phe | Val | Gln | Gln | His | |
| | | | 150 | | | | | 155 | | | | | 160 | | | |

| cag | gct | gaa | aaa | aca | gaa | cga | gag | aat | cgg | ctt | aaa | gag | ttt | tac | acc | 826 |
|---|---|---|---|---|---|---|---|---|---|---|---|---|---|---|---|---|
| Gln | Ala | Glu | Lys | Thr | Glu | Arg | Glu | Asn | Arg | Leu | Lys | Glu | Phe | Tyr | Thr | |
| | | 165 | | | | | 170 | | | | | 175 | | | | |

| agg | gag | tat | gaa | aag | ctt | cgg | gac | act | tac | att | gaa | gaa | gca | gag | aag | 874 |
|---|---|---|---|---|---|---|---|---|---|---|---|---|---|---|---|---|
| Arg | Glu | Tyr | Glu | Lys | Leu | Arg | Asp | Thr | Tyr | Ile | Glu | Glu | Ala | Glu | Lys | |
| | 180 | | | | | 185 | | | | | 190 | | | | | |

| tac | aaa | atg | caa | ttg | caa | gag | cag | ttt | gac | aac | tta | aat | gcg | cat | gaa | 922 |
|---|---|---|---|---|---|---|---|---|---|---|---|---|---|---|---|---|
| Tyr | Lys | Met | Gln | Leu | Gln | Glu | Gln | Phe | Asp | Asn | Leu | Asn | Ala | His | Glu | |
| 195 | | | | | 200 | | | | | 205 | | | | | 210 | |

| acc | tct | aag | ttg | gaa | att | gaa | gct | agc | cac | tca | gag | aaa | ctt | gaa | ttg | 970 |
|---|---|---|---|---|---|---|---|---|---|---|---|---|---|---|---|---|
| Thr | Ser | Lys | Leu | Glu | Ile | Glu | Ala | Ser | His | Ser | Glu | Lys | Leu | Glu | Leu | |
| | | | | 215 | | | | | 220 | | | | | 225 | | |

| cta | aag | aag | gcc | tat | gaa | gcc | tcc | ctt | tca | gaa | att | aag | aaa | ggc | cat | 1018 |
|---|---|---|---|---|---|---|---|---|---|---|---|---|---|---|---|---|
| Leu | Lys | Lys | Ala | Tyr | Glu | Ala | Ser | Leu | Ser | Glu | Ile | Lys | Lys | Gly | His | |
| | | | 230 | | | | | 235 | | | | | 240 | | | |

| gaa | ata | gaa | aag | aaa | tcg | ctt | gaa | gat | tta | ctt | tct | gag | aag | cag | gaa | 1066 |
|---|---|---|---|---|---|---|---|---|---|---|---|---|---|---|---|---|
| Glu | Ile | Glu | Lys | Lys | Ser | Leu | Glu | Asp | Leu | Leu | Ser | Glu | Lys | Gln | Glu | |
| | | 245 | | | | | 250 | | | | | 255 | | | | |

| tcg | cta | gag | aag | caa | atc | aat | gat | ctg | aag | agt | gaa | aat | gat | gct | tta | 1114 |
|---|---|---|---|---|---|---|---|---|---|---|---|---|---|---|---|---|
| Ser | Leu | Glu | Lys | Gln | Ile | Asn | Asp | Leu | Lys | Ser | Glu | Asn | Asp | Ala | Leu | |
| | 260 | | | | | 265 | | | | | 270 | | | | | |

| aat | gaa | aaa | ttg | aaa | tca | gaa | gaa | caa | aaa | aga | aga | gca | aga | gaa | aaa | 1162 |
|---|---|---|---|---|---|---|---|---|---|---|---|---|---|---|---|---|
| Asn | Glu | Lys | Leu | Lys | Ser | Glu | Glu | Gln | Lys | Arg | Arg | Ala | Arg | Glu | Lys | |
| 275 | | | | | 280 | | | | | 285 | | | | | 290 | |

| gca | aat | ttg | aaa | aat | cct | cag | atc | atg | tat | cta | gaa | cag | gag | tta | gaa | 1210 |
|---|---|---|---|---|---|---|---|---|---|---|---|---|---|---|---|---|
| Ala | Asn | Leu | Lys | Asn | Pro | Gln | Ile | Met | Tyr | Leu | Glu | Gln | Glu | Leu | Glu | |
| | | | | 295 | | | | | 300 | | | | | 305 | | |

| agc | ctg | aaa | gct | gtg | tta | gag | atc | aag | aat | gag | aaa | ctg | cat | caa | cag | 1258 |
|---|---|---|---|---|---|---|---|---|---|---|---|---|---|---|---|---|
| Ser | Leu | Lys | Ala | Val | Leu | Glu | Ile | Lys | Asn | Glu | Lys | Leu | His | Gln | Gln | |
| | | | 310 | | | | | 315 | | | | | 320 | | | |

| gac | atc | aag | tta | atg | aaa | atg | gag | aaa | ctg | gtg | gac | aac | aac | aca | gca | 1306 |
|---|---|---|---|---|---|---|---|---|---|---|---|---|---|---|---|---|
| Asp | Ile | Lys | Leu | Met | Lys | Met | Glu | Lys | Leu | Val | Asp | Asn | Asn | Thr | Ala | |
| | | 325 | | | | | 330 | | | | | 335 | | | | |

| ttg | gtt | gac | aaa | ttg | aag | cgt | ttc | cag | cag | gag | aat | gaa | gaa | ttg | aaa | 1354 |
|---|---|---|---|---|---|---|---|---|---|---|---|---|---|---|---|---|
| Leu | Val | Asp | Lys | Leu | Lys | Arg | Phe | Gln | Gln | Glu | Asn | Glu | Glu | Leu | Lys | |
| | 340 | | | | | 345 | | | | | 350 | | | | | |

| gct | cgg | atg | gac | aag | cac | atg | gca | atc | tca | agg | cag | ctt | tcc | acg | gag | 1402 |
|---|---|---|---|---|---|---|---|---|---|---|---|---|---|---|---|---|
| Ala | Arg | Met | Asp | Lys | His | Met | Ala | Ile | Ser | Arg | Gln | Leu | Ser | Thr | Glu | |
| 355 | | | | | 360 | | | | | 365 | | | | | 370 | |

| cag | gct | gtt | ctg | caa | gag | tcg | ctg | gag | aag | gag | tcg | aaa | gtc | aac | aag | 1450 |
|---|---|---|---|---|---|---|---|---|---|---|---|---|---|---|---|---|
| Gln | Ala | Val | Leu | Gln | Glu | Ser | Leu | Glu | Lys | Glu | Ser | Lys | Val | Asn | Lys | |
| | | | | 375 | | | | | 380 | | | | | 385 | | |

| cga | ctc | tct | atg | gaa | aac | gag | gag | ctt | ctg | tgg | aaa | ctg | cac | aat | ggg | 1498 |
|---|---|---|---|---|---|---|---|---|---|---|---|---|---|---|---|---|
| Arg | Leu | Ser | Met | Glu | Asn | Glu | Glu | Leu | Leu | Trp | Lys | Leu | His | Asn | Gly | |
| | | | 390 | | | | | 395 | | | | | 400 | | | |

| gac | ctg | tgt | agc | ccc | aag | aga | tcc | ccc | aca | tcc | tcc | gcc | atc | cct | ttg | 1546 |
|---|---|---|---|---|---|---|---|---|---|---|---|---|---|---|---|---|
| Asp | Leu | Cys | Ser | Pro | Lys | Arg | Ser | Pro | Thr | Ser | Ser | Ala | Ile | Pro | Leu | |
| | | 405 | | | | | 410 | | | | | 415 | | | | |

| cag | tca | cca | agg | aat | tcg | ggc | tcc | ttc | cct | agc | ccc | agc | att | tca | ccc | 1594 |
|---|---|---|---|---|---|---|---|---|---|---|---|---|---|---|---|---|
| Gln | Ser | Pro | Arg | Asn | Ser | Gly | Ser | Phe | Pro | Ser | Pro | Ser | Ile | Ser | Pro | |
| | 420 | | | | | 425 | | | | | 430 | | | | | |

-continued

| | |
|---|---|
| aga tga cacgtcccca aagtccacag actctctgaa agcattttga tgcaggtctg | 1650 |
| Arg * | |
| 435 | |
| caggactgac cccaaggagg aacgtgggca agagggtat atcagcacac gtgtgatcac | 1710 |
| cgtaggtaac tggagcgtca ccaccggcgg aatcgagctt ctgagactgg aagtctggag | 1770 |
| gaagactttt gcctccgtcc aaaagattcc tccaaaaaaa gatttaaaaa agatttcgg | 1830 |
| catcgacacg gacgttgttg cacaaagcac ttaaagaacg agagcatctt gttcattgcc | 1890 |
| ttttcacct aagcataagg ggaaaaactc tcagggccct attaagattt ataacctttg | 1950 |
| taatgttctt caccacagac accttcttgt gagttttcag tctgactgtg ggggtggggg | 2010 |
| gtgtgaatga aatggatgtc acagagtgtc atgtgtctga tgcagcctcc tctgctgtgt | 2070 |
| attaaatgtc aaaatctgaa tatatctgga tatgtactaa tcaaataata atcaatcaat | 2130 |
| cagcatatac atttcagcca aagccataga agaaaaagca atagttgctt gaattatgat | 2190 |
| catctaccac caactctgct cagccctgta acagggtagg gagagggtat aacaggaaga | 2250 |
| gctttgactt gtccctgtct atacattctc tgtatctttt gggggtaact tcttggcagt | 2310 |
| ttttcagtgt tcagccatgt cagttgaaac tagattttc tgtagatttt ttacttaccc | 2370 |
| atgtgagcct aacactatcc tgtaattcat tttctcaggc tatgtgtaaa tgtagaaccc | 2430 |
| taatttttct ataaaaaaac aaactaacta actgtgtaaa gaaagaaaaa gggaagtacc | 2490 |
| aatgggtttt tccaccttat ttttaccttt gatctaccct tgcagattta acctgtcttc | 2550 |
| ttccctccca ttattctcat tttccttta cctttctcca ccatccgagc ccacaaaagc | 2610 |
| aaaccttcta cctcctacct actttttctct gggacaagga taaggaata tgattttcca | 2670 |
| gagccccaga gccagctcat cttccaggtg ctgaaaccac tttccaaata aactaaagcc | 2730 |
| tggatttgat attacaaatt ttgggaaatc ttagaataaa gaacgagaac aaggaagtca | 2790 |
| ttggctagta taattaagaa aggtaggatt cagtgcttac cgatgatgca gtacttgata | 2850 |
| gaagaaaaca gtctgggagg atagcgctca ttttttcagtt acccttttaag gagtcccttt | 2910 |
| gtctttggga aagtagcaga atggtccgct tctttcccat gagtggaaaa tgtggcttgt | 2970 |
| ccaactctcc tccaggttgc atttcagttt cttttccaaaa cttattaccct cccctaatcc | 3030 |
| tgagactttg gaaaggtgg aaggaagaac tgttgctta tctcccctc cctgcatgtg | 3090 |
| tcaacattgt gatgtcagta tttactaatc tacattcagt ggctgtacaa ataacagctg | 3150 |
| tagtaagaag agattcagga tgctagaggt gaatatttgg gtcatttaca tgtacactac | 3210 |
| atagcaagtt gatactcatg ttgcatgttc ttttaaatta gtgattttgt gtcttaagtc | 3270 |
| tttaacttcc aatacttcat catgtatgta accttccatg tttgcttctg ataaatggaa | 3330 |
| atgtaggttc actgccactt catgagatat ctctgctcac gcttccaagt tgttctcaat | 3390 |
| gacattagcc aaagttgggt ttgccattca tccctaggc atggtaaatc ttgtgttgtt | 3450 |
| ccctgctgtc ctccgtatta cgtgaccggc aaataaatct catagcagtt aatataaaac | 3510 |
| atctttggag gatgggagag aacaggaggg aagatgggaa acaaataga gaattcttaa | 3570 |
| gattttgttt aaaccaaatg tttcatgtag aatgcaaaat gttggcacgt caaaaatatg | 3630 |
| aatgtgtaga caactgtagt tgtgctcagt ttgtagtgat gggaagtgta ttttactctg | 3690 |
| atcaaataaa taatgctgga atactcaaaa aaaaaaaaaa aaaaaaaaaa aa | 3742 |

<210> SEQ ID NO 8
<211> LENGTH: 435
<212> TYPE: PRT
<213> ORGANISM: Homo sapiens

```
<400> SEQUENCE: 8

Met Leu Leu Ser Pro Lys Phe Ser Leu Ser Thr Ile His Ile Arg Leu
  1               5                  10                  15

Thr Ala Lys Gly Leu Leu Arg Asn Leu Arg Leu Pro Ser Gly Phe Arg
             20                  25                  30

Arg Ser Thr Val Val Phe His Thr Val Glu Lys Ser Arg Gln Lys Asn
         35                  40                  45

Pro Arg Ser Leu Cys Ile Gln Pro Gln Thr Ala Pro Asp Ala Leu Pro
     50                  55                  60

Pro Glu Lys Thr Leu Glu Leu Thr Gln Tyr Lys Thr Lys Cys Glu Asn
 65                  70                  75                  80

Gln Ser Gly Phe Ile Leu Gln Leu Lys Gln Leu Leu Ala Cys Gly Asn
                 85                  90                  95

Thr Lys Phe Glu Ala Leu Thr Val Val Ile Gln His Leu Leu Ser Glu
             100                 105                 110

Arg Glu Glu Ala Leu Lys Gln His Lys Thr Leu Ser Gln Glu Leu Val
         115                 120                 125

Asn Leu Arg Gly Glu Leu Val Thr Ala Ser Thr Thr Cys Glu Lys Leu
    130                 135                 140

Glu Lys Ala Arg Asn Glu Leu Gln Thr Val Tyr Glu Ala Phe Val Gln
145                 150                 155                 160

Gln His Gln Ala Glu Lys Thr Glu Arg Glu Asn Arg Leu Lys Glu Phe
                165                 170                 175

Tyr Thr Arg Glu Tyr Glu Lys Leu Arg Asp Thr Tyr Ile Glu Glu Ala
            180                 185                 190

Glu Lys Tyr Lys Met Gln Leu Gln Glu Gln Phe Asp Asn Leu Asn Ala
        195                 200                 205

His Glu Thr Ser Lys Leu Glu Ile Glu Ala Ser His Ser Gly Lys Leu
    210                 215                 220

Glu Leu Leu Lys Lys Ala Tyr Glu Ala Ser Leu Ser Glu Ile Lys Lys
225                 230                 235                 240

Gly His Glu Ile Glu Lys Lys Ser Leu Glu Asp Leu Leu Ser Glu Lys
                245                 250                 255

Gln Glu Ser Leu Glu Lys Gln Ile Asn Asp Leu Lys Ser Glu Asn Asp
            260                 265                 270

Ala Leu Asn Glu Lys Leu Lys Ser Glu Glu Gln Lys Arg Arg Ala Arg
        275                 280                 285

Glu Lys Ala Asn Leu Lys Asn Pro Gln Ile Met Tyr Leu Glu Gln Glu
    290                 295                 300

Leu Glu Ser Leu Lys Ala Val Leu Glu Ile Lys Asn Glu Lys Leu His
305                 310                 315                 320

Gln Gln Asp Ile Lys Leu Met Lys Met Glu Lys Leu Val Asp Asn Asn
                325                 330                 335

Thr Ala Leu Val Asp Lys Leu Lys Arg Phe Gln Gln Glu Asn Glu Glu
            340                 345                 350

Leu Lys Ala Arg Met Asp Lys His Met Ala Ile Ser Arg Gln Leu Ser
        355                 360                 365

Thr Glu Gln Ala Val Leu Gln Glu Ser Leu Glu Lys Glu Ser Lys Val
    370                 375                 380

Asn Lys Arg Leu Ser Met Glu Asn Glu Glu Leu Leu Trp Lys Leu His
385                 390                 395                 400

Asn Gly Asp Leu Cys Ser Pro Lys Arg Ser Pro Thr Ser Ser Ala Ile
```

```
                     405                 410                 415
         Pro Leu Gln Ser Pro Arg Asn Ser Gly Ser Phe Pro Ser Pro Ser Ile
                 420                 425                 430

Ser Pro Arg
                 435

<210> SEQ ID NO 9
<211> LENGTH: 1308
<212> TYPE: DNA
<213> ORGANISM: Homo sapiens
<220> FEATURE:
<221> NAME/KEY: CDS
<222> LOCATION: (1)...(1308)

<400> SEQUENCE: 9 atg ttg ttg tct ccc aaa ttc tcc tta tcc acc att cac ata cga ctg         48
Met Leu Leu Ser Pro Lys Phe Ser Leu Ser Thr Ile His Ile Arg Leu
1               5                  10                  15 acg gcc aaa gga ttg ctt cga aac ctt cga ctt cct tca ggg ttt agg         96
Thr Ala Lys Gly Leu Leu Arg Asn Leu Arg Leu Pro Ser Gly Phe Arg
                20                  25                  30 aga agc act gtt gtt ttc cac aca gtt gaa aag agc agg caa aag aat        144
Arg Ser Thr Val Val Phe His Thr Val Glu Lys Ser Arg Gln Lys Asn
            35                  40                  45 cct cga agc tta tgt atc cag cca cag aca gct ccc gat gcg ctg ccc        192
Pro Arg Ser Leu Cys Ile Gln Pro Gln Thr Ala Pro Asp Ala Leu Pro
        50                  55                  60 cct gag aaa aca ctt gaa ttg acg caa tat aaa aca aaa tgt gaa aac        240
Pro Glu Lys Thr Leu Glu Leu Thr Gln Tyr Lys Thr Lys Cys Glu Asn
65                  70                  75                  80 caa agt gga ttt atc ctg cag ctc aag cag ctt ctt gcc tgt ggt aat        288
Gln Ser Gly Phe Ile Leu Gln Leu Lys Gln Leu Leu Ala Cys Gly Asn
                85                  90                  95 acc aag ttt gag gca ttg aca gtt gtg att cag cac ctg ctg tct gag        336
Thr Lys Phe Glu Ala Leu Thr Val Val Ile Gln His Leu Leu Ser Glu
                100                 105                 110 cgg gag gaa gca ctg aaa caa cac aaa acc cta tct caa gaa ctt gtt        384
Arg Glu Glu Ala Leu Lys Gln His Lys Thr Leu Ser Gln Glu Leu Val
            115                 120                 125 aac ctc cgg gga gag cta gtc act gct tca acc acc tgt gag aaa tta        432
Asn Leu Arg Gly Glu Leu Val Thr Ala Ser Thr Thr Cys Glu Lys Leu
        130                 135                 140 gaa aaa gcc agg aat gag tta caa aca gtg tat gaa gca ttc gtc cag        480
Glu Lys Ala Arg Asn Glu Leu Gln Thr Val Tyr Glu Ala Phe Val Gln
145                 150                 155                 160 cag cac cag gct gaa aaa aca gaa cga gag aat cgg ctt aaa gag ttt        528
Gln His Gln Ala Glu Lys Thr Glu Arg Glu Asn Arg Leu Lys Glu Phe
                165                 170                 175 tac acc agg gag tat gaa aag ctt cgg gac act tac att gaa gaa gca        576
Tyr Thr Arg Glu Tyr Glu Lys Leu Arg Asp Thr Tyr Ile Glu Glu Ala
                180                 185                 190 gag aag tac aaa atg caa ttg caa gag cag ttt gac aac tta aat gcg        624
Glu Lys Tyr Lys Met Gln Leu Gln Glu Gln Phe Asp Asn Leu Asn Ala
            195                 200                 205 cat gaa acc tct aag ttg gaa att gaa gct agc cac tca gag aaa ctt        672
His Glu Thr Ser Lys Leu Glu Ile Glu Ala Ser His Ser Glu Lys Leu
        210                 215                 220 gaa ttg cta aag aag gcc tat gaa gcc tcc ctt tca gaa att aag aaa        720
Glu Leu Leu Lys Lys Ala Tyr Glu Ala Ser Leu Ser Glu Ile Lys Lys
225                 230                 235                 240
```

-continued

```
ggc cat gaa ata gaa aag aaa tcg ctt gaa gat tta ctt tct gag aag        768
Gly His Glu Ile Glu Lys Lys Ser Leu Glu Asp Leu Leu Ser Glu Lys
            245                 250                 255 cag gaa tcg cta gag aag caa atc aat gat ctg aag agt gaa aat gat        816
Gln Glu Ser Leu Glu Lys Gln Ile Asn Asp Leu Lys Ser Glu Asn Asp
        260                 265                 270 gct tta aat gaa aaa ttg aaa tca gaa gaa caa aaa aga aga gca aga        864
Ala Leu Asn Glu Lys Leu Lys Ser Glu Glu Gln Lys Arg Arg Ala Arg
    275                 280                 285 gaa aaa gca aat ttg aaa aat cct cag atc atg tat cta gaa cag gag        912
Glu Lys Ala Asn Leu Lys Asn Pro Gln Ile Met Tyr Leu Glu Gln Glu
290                 295                 300 tta gaa agc ctg aaa gct gtg tta gag atc aag aat gag aaa ctg cat        960
Leu Glu Ser Leu Lys Ala Val Leu Glu Ile Lys Asn Glu Lys Leu His
305                 310                 315                 320 caa cag gac atc aag tta atg aaa atg gag aaa ctg gtg gac aac aac       1008
Gln Gln Asp Ile Lys Leu Met Lys Met Glu Lys Leu Val Asp Asn Asn
                325                 330                 335 aca gca ttg gtt gac aaa ttg aag cgt ttc cag cag gag aat gaa gaa       1056
Thr Ala Leu Val Asp Lys Leu Lys Arg Phe Gln Gln Glu Asn Glu Glu
            340                 345                 350 ttg aaa gct cgg atg gac aag cac atg gca atc tca agg cag ctt tcc       1104
Leu Lys Ala Arg Met Asp Lys His Met Ala Ile Ser Arg Gln Leu Ser
        355                 360                 365 acg gag cag gct gtt ctg caa gag tcg ctg gag aag gag tcg aaa gtc       1152
Thr Glu Gln Ala Val Leu Gln Glu Ser Leu Glu Lys Glu Ser Lys Val
    370                 375                 380 aac aag cga ctc tct atg gaa aac gag gag ctt ctg tgg aaa ctg cac       1200
Asn Lys Arg Leu Ser Met Glu Asn Glu Glu Leu Leu Trp Lys Leu His
385                 390                 395                 400 aat ggg gac ctg tgt agc ccc aag aga tcc ccc aca tcc tcc gcc atc       1248
Asn Gly Asp Leu Cys Ser Pro Lys Arg Ser Pro Thr Ser Ser Ala Ile
                405                 410                 415 cct ttg cag tca cca agg aat tcg ggc tcc ttc cct agc ccc agc att       1296
Pro Leu Gln Ser Pro Arg Asn Ser Gly Ser Phe Pro Ser Pro Ser Ile
            420                 425                 430 tca ccc aga tga                                                       1308
Ser Pro Arg  *
        435
```

<210> SEQ ID NO 10
<211> LENGTH: 435
<212> TYPE: PRT
<213> ORGANISM: Homo sapiens

<400> SEQUENCE: 10

```
Met Leu Leu Ser Pro Lys Phe Ser Leu Ser Thr Ile His Ile Arg Leu
 1               5                  10                  15

Thr Ala Lys Gly Leu Leu Arg Asn Leu Arg Leu Pro Ser Gly Phe Arg
            20                  25                  30

Arg Ser Thr Val Val Phe His Thr Val Glu Lys Ser Arg Gln Lys Asn
        35                  40                  45

Pro Arg Ser Leu Cys Ile Gln Pro Gln Thr Ala Pro Asp Ala Leu Pro
    50                  55                  60

Pro Glu Lys Thr Leu Glu Leu Thr Gln Tyr Lys Thr Lys Cys Glu Asn
65                  70                  75                  80

Gln Ser Gly Phe Ile Leu Gln Leu Lys Gln Leu Leu Ala Cys Gly Asn
                85                  90                  95

Thr Lys Phe Glu Ala Leu Thr Val Val Ile Gln His Leu Leu Ser Glu
```

```
                    100                 105                 110
Arg Glu Glu Ala Leu Lys Gln His Lys Thr Leu Ser Gln Glu Leu Val
            115                 120                 125

Asn Leu Arg Gly Glu Leu Val Thr Ala Ser Thr Thr Cys Glu Lys Leu
        130                 135                 140

Glu Lys Ala Arg Asn Glu Leu Gln Thr Val Tyr Glu Ala Phe Val Gln
145                 150                 155                 160

Gln His Gln Ala Glu Lys Thr Glu Arg Glu Asn Arg Leu Lys Glu Phe
                165                 170                 175

Tyr Thr Arg Glu Tyr Glu Lys Leu Arg Asp Thr Tyr Ile Glu Glu Ala
            180                 185                 190

Glu Lys Tyr Lys Met Gln Leu Gln Glu Gln Phe Asp Asn Leu Asn Ala
        195                 200                 205

His Glu Thr Ser Lys Leu Glu Ile Glu Ala Ser His Ser Glu Lys Leu
    210                 215                 220

Glu Leu Leu Lys Lys Ala Tyr Glu Ala Ser Leu Ser Glu Ile Lys Lys
225                 230                 235                 240

Gly His Glu Ile Glu Lys Lys Ser Leu Glu Asp Leu Leu Ser Glu Lys
                245                 250                 255

Gln Glu Ser Leu Glu Lys Gln Ile Asn Asp Leu Lys Ser Glu Asn Asp
            260                 265                 270

Ala Leu Asn Glu Lys Leu Lys Ser Glu Glu Gln Lys Arg Arg Ala Arg
        275                 280                 285

Glu Lys Ala Asn Leu Lys Asn Pro Gln Ile Met Tyr Leu Glu Gln Glu
    290                 295                 300

Leu Glu Ser Leu Lys Ala Val Leu Glu Ile Lys Asn Glu Lys Leu His
305                 310                 315                 320

Gln Gln Asp Ile Lys Leu Met Lys Met Glu Lys Leu Val Asp Asn Asn
                325                 330                 335

Thr Ala Leu Val Asp Lys Leu Lys Arg Phe Gln Gln Glu Asn Glu Glu
            340                 345                 350

Leu Lys Ala Arg Met Asp Lys His Met Ala Ile Ser Arg Gln Leu Ser
        355                 360                 365

Thr Glu Gln Ala Val Leu Gln Glu Ser Leu Glu Lys Glu Ser Lys Val
    370                 375                 380

Asn Lys Arg Leu Ser Met Glu Asn Glu Glu Leu Leu Trp Lys Leu His
385                 390                 395                 400

Asn Gly Asp Leu Cys Ser Pro Lys Ser Pro Thr Ser Ser Ala Ile
                405                 410                 415

Pro Leu Gln Ser Pro Arg Asn Ser Gly Ser Phe Pro Ser Pro Ser Ile
            420                 425                 430

Ser Pro Arg
        435

<210> SEQ ID NO 11
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 11
cgcggatccc agacagaccg gacggaactg gag                              33

<210> SEQ ID NO 12
```

-continued

```
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 12
ccggaattca ctacaacctt tcgtttaaag catc                                   34
```

NUCLEIC SEQUENCES CODING FOR AN AT2 INTERACTING PROTEINS INTERACTING WITH THE AT2 RECEPTOR AND THEIR APPLICATIONS

The present invention relates to nucleic sequences encoding a protein capable of interacting with the AT2 receptor, to oligonucleotides contained in the said sequences, to their applications as probes and for the expression of the said proteins, to the vectors useful for the said expression, to the host cells containing the said vectors and to a model for studying the AT2 receptor.

The present invention also relates to the said proteins and to their applications.

The octapeptide, angiotensin II, mainly known as a regulator of blood pressure, has also been described as an important modulator of cell growth. Interestingly, this peptide appears to exert opposite effects on cell growth according to whether it is bound to one or the other of its two subtypes of membrane receptors (AT1 or AT2).

The AT2 receptor subtype, which also belongs to the G protein-coupled receptor family, is still poorly characterized both from the point of view of its mechanisms of activation and its physiological role (C. Nahmias et al., *Trends Pharmacol Sci,* 1995, 16, 223–225). Several arguments suggest, however, a role for this receptor in the phenomena of cell proliferation, differentiation or adhesion.

The AT2 receptor is highly expressed during foetal life, disappears in adults in most tissues, but becomes reexpressed under pathophysiological conditions involving restructuring of the tissues.

Studies carried out in vivo have demonstrated the inhibitory role exerted by the AT2 subtype on the proliferation of the muscle cells of the tunica intima vasorum after vascular lesion (P. Janiak et al., *Hypertension,* 1992, 20, 737–745; M Nakajima et al., *Proc. Natl. Acad. Sci. USA,* 1995, 92, 10663–10667).

Moreover, the stimulati on of the AT2 receptor activates phosphatase SHP-1 (Bedecs K., et al; *Biochem. J.,* 1997, 325, 449–454). The fact that the AT2 receptor activates a phosphatase is consistent with its antiproliferative effects.

In the light of the above, it has been shown that, on cells in culture, the AT2 receptor:
  inhibits the synthesis of DNA and proliferation, which are induced by angiotensin II (Ang II) and bFGF (M. Stoll et al., *J. Clin. Invest.,* 1995, 95, 651–657),
  induces apoptosis (T. Yamada et al., *Proc. Natl. Acad. Sci. USA,* 1996, 93, 156–160), and
  induces neuronal differentiation (L. Laflamme et al., *J. Biol. Chem.,* 1996, 271, 22729–22735).

Studies of the signalling pathways associated with the AT2 receptor have been undertaken in cells of the N1E-115 line which are derived from a murine neuroblastoma and which express only the AT2 subtype. A first study has made it possible to demonstrate rapid and transient dephosphorylation of some proteins on the tyrosine residues following the treatment of N1E-115 cells with angiotensin II (C. Nahmias et al., *Biochem. J.,* 1995, 306, 87–92). It has also been shown that the AT2 receptor interferes with the pathways for activation of growth factor receptors and inhibits the activity of MAP kinases (ERK1 and ERK2). (mitoqen-activated protein), which play a key role in the phenomena of cell proliferation and differentiation. The inhibitory effect of AT2 on the activation of MAP kinases is rapid and transient, does not involve a regulatory protein sensitive to the pertussis toxin (of the Gi/Go type), but involves the activation of an orthovanadate-sensitive tyrosine phosphatase.

Taking into account the role of the AT2 receptor in cell proliferation, the inventors have sought to develop tools capable of regulating the action of the AT2 receptor. Indeed, the activation of the AT2 receptor may have repercussions in cancerology (inhibition of cell proliferation).

In general, the AT2 receptor has opposite effects to those of AT1 on the activation of MAP kinases and on cell proliferation; study of the communication which may exist between these two receptor subtypes, which bind the same ligand, is consequently of interest.

The study of the signalling pathways and of the regulation of the AT2 receptor also represents a major stake for human health knowing that antagonists of the AT1 receptor are currently administered to patients with hypertension. In this context, it is essential to know the biological effects associated with the AT2 receptor which remains activable by circulating Ang II in this type of treatment.

The subject of the present invention is an isolated nucleic acid (DNA or RNA) fragment, encoding a protein capable of binding to the AT2 receptor, which fragment is selected from the group consisting of the sequences SEQ ID NO:1, 3, 5, 7 and 9, as represented in the sequence listing included in the present application.

These various sequences correspond to the complementary DNA (cDNA) encoding all or part of the protein called hereinafter ATIP (AT2 interacting protein).

The sequence SEQ ID NO:1 (1803 bp) corresponds to the complete nucleic sequence of mouse ATIP and includes both the parts encoding the AT2 receptor binding protein and the noncoding parts.

The sequence NO:3 (1323 bp) corresponds to the nucleic acid sequence of the coding part of the sequence SEQ ID NO:1, while the sequence SEQ ID NO:5 corresponds to the sequence NO:1 fragment obtained by the two-hybrid technique (A Plessis et al., M/S, 1994, 9, I-1K; J. Luban et al., *Curr. Op. Biotechnol.,* 1995, 6, 59–64).

The sequence SEQ ID NO:7 (3742 bp) corresponds to the complete nucleic sequence of the human cDNA and includes both the parts encoding the protein homologous to the mouse ATIP and the noncoding parts.

The sequence SEQ ID NO:9 (1308 bp) corresponds to the coding part of the sequence SEQ ID NO:7.

The subject of the present invention is also transcripts, characterized in that they are complementary to the sequences in accordance with the invention and are in particular generated from the said sequences.

The subject of the present invention is, in addition, fragments of the said sequences comprising between 20 and 400 bp, useful as probes or as primers, for the detection of the sequences SEQ ID NO:1, 3, 5, 7 or 9, or of homologous sequences.

Among the said fragments, there may be mentioned in particular a probe of 354 bp (SEQ ID NO:5) as well as any fragment of 20 bp to 400 bp included in the sequences SEQ ID NO:1, 3, 5, 7 or 9.

As primer, there will be used in particular the sequence SEQ ID NO:10 (antisense oligonucleotide) which makes it possible in particular to amplify the 5' parts of the various mRNAs corresponding to ATIP (5' RACE technique: Marathon cDNA amplification kit, Clontech).

It is also possible to use, as amplification primers, any pair of oligonucleotides of more than 20 bp and comprising part of the ATIP (human or mouse) nucleic sequence, in particular the pair SEQ ID NO:11–SEQ ID NO:12.

The preferred hybridization (prehybridization and hybridization) conditions are in particular the following: 45% formamide, 9% dextran sulphate, 0.2% BSA, 0.2% polyvinyl pyrrolidone, 0.2% Ficoll, 0.1% sodium pyrophosphate, 0.01% SDS, 0.05 mM Tris pH 7.5, 0.9 M NaCl and rinses to a stringency corresponding to the buffer: 1×SSC, 0.1% SDS.

The subject of the present invention is also a purified and isolated protein, called ATIP, which is capable of interacting with the AT2 receptor and which is selected from the group consisting of the sequences SEQ ID NO:2, 4, 6 or 8.

The murine and human sequences exhibit 85.6% homologies. The human sequence (human ATIP) possesses 5 amino acids less than the mouse sequence (mouse ATIP). The amino acids missing from the human sequence are situated at the level of amino acids: 162, 163, 164, 166 and 214 of the mouse ATIP sequence.

Comparisons (Blast) between the ATIP protein sequences according to the invention and the sequences contained in data banks indicate that human ATIP (like mouse ATIP) never exhibits more than 25% homology with a known sequence, and this being the case only over part of this sequence.

The subject of the present invention is also a translational product, characterized in that it is encoded by a nucleotide sequence in accordance with the invention.

The subject of the present invention is, in addition, antibodies, characterized in that they are directed against the ATIP protein or an ATIP protein fragment according to the invention.

The subject of the present invention is also a recombinant cloning and/or expression vector, characterized in that it comprises a nucleotide sequence in accordance with the invention.

The subject of the present invention is also a transformed host cell, characterized in that it comprises a vector as defined above.

Among the preferred transformed cells according to the invention, there may be mentioned E. coli and CHO cells.

The subject of the present invention is also transformed host cells, characterized in that they consist of a suitable yeast strain cotransformed with at least two vectors which respectively encode (i) a so-called bait protein selected from the group consisting of a fragment containing at least SEQ ID NO:5 of the ATIP protein and a fragment containing at least the C-terminal end of the AT2 receptor, which bait protein is fused with a protein selected from the group consisting of the DNA-binding domain of a transcription factor and the activation domain of the same transcription factor and (ii) a so-called prey protein, selected from the group consisting of a fragment containing at least SEQ ID NO:5 of the ATIP protein, a fragment containing at least the C-terminal end of the AT2 receptor and any other polypeptide corresponding to a sequence contained in a cDNA library, which prey protein is fused with a protein selected from the group consisting of the DNA-binding domain of a transcription factor and the activation domain of the same transcription factor, which vectors comprise, in addition, selectable markers.

According to an advantageous embodiment of the said cells, they consist in particular of:

either a suitable yeast strain cotransformed with three vectors which respectively encode (i) a bait corresponding to a fragment containing the C-terminal end of the AT2 receptor fused with a protein selected from the group consisting of the DNA-binding domain of a transcription factor and the activation domain of the said transcription factor, (ii) a fragment containing at least SEQ ID NO:5 of the ATIP protein according to the invention, fused with a protein selected from the group consisting of the DNA-binding domain of a transcription factor and the activation domain of the said transcription factor and (iii) a polypeptide corresponding to a sequence contained in a cDNA library, which vectors comprise, in addition, selectable markers, or a suitable yeast strain cotransformed with two vectors which respectively encode (i) a fragment containing at least SEQ ID NO:5 of the ATIP protein according to the invention, fused with a protein selected from the group consisting of the DNA-binding domain of a transcription factor and the activation domain of the said transcription factor and (ii) a polypeptide corresponding to a sequence contained in a cDNA library, fused with a protein selected from the group consisting of the DNA-binding domain of the transcription factor and the activation domain of the said transcription factor, which vectors comprise, in addition, selectable markers, or a suitable yeast strain cotransformed with two vectors, namely (i) a vector encoding a fragment containing at least SEQ ID NO:5 of the ATIP protein, mutated or not, fused with a protein selected from the group consisting of the DNA-binding domain of a transcription factor and the activation domain of the said transcription factor and (ii) a vector encoding a fragment containing the C-terminal end of the AT2 receptor, mutated or not, fused with a protein selected from the group consisting of the DNA-binding domain of a transcription factor and the activation domain of the said transcription factor, which vectors comprise, in addition, selectable markers, one of the two vectors necessarily encoding a mutated protein.

The subject of the present invention is also a method for selecting proteins inhibiting ATIP protein according to the invention-AT2 receptor interaction, which method comprises:

(a) cotransforming a suitable yeast strain with three vectors which respectively encode (i) a bait corresponding to a fragment containing the C-terminal end of the AT2 receptor fused with a protein selected from the group consisting of the DNA-binding domain of a transcription factor and the activation domain of the said transcription factor, (ii) a fragment containing at least SEQ ID NO:5 of the ATIP protein according to the invention, fused with a protein selected from the group consisting of the DNA-binding domain of a transcription factor and the activation domain of the said transcription factor and (iii) a polypeptide corresponding to a sequence contained in a cDNA library, which vectors comprise, in addition, selectable markers, (b) selecting the clones of cDNA library expressing a polypeptide inhibiting the AT2 receptor-ATIP protein according to the invention interaction, on an appropriate selective medium, and (c) identifying the said polypeptide.

Such a method uses in particular the so-called reverse two-hybrid or three-hybrid technique as described in Vidal et al. (*Proc. Natl. Acad. Sci. USA,* 1996, 93, 10315–10320 and 10321–10326) or Tirode et al. (*J. Biol. Chem.,* 1997, 272, 37, 22995–22999).

The subject of the present invention is also a method for screening polypeptides interacting with the ATIP protein according to the invention, which method comprises:

(a) cotransforming a suitable yeast strain with two vectors as defined above, namely which respectively encode (i) a fragment containing at least SEQ ID NO:5 of the ATIP protein according to the invention, fused with a protein selected from the group consisting of the DNA-binding domain of a transcription factor and the activation domain of the said transcription factor and (ii) a polypeptide corresponding to a sequence contained in a cDNA library, fused with a protein selected from the group consisting of the DNA-binding domain of a transcription factor and the activation domain of the said transcription factor, which vectors comprise, in addition, selectable markers, and (b) selecting the clones expressing a polypeptide interacting with the ATIP protein, on a suitable selective medium.

Such a method makes it possible in particular to search for other proteins interacting with the ATIP protein, in particular in order to find the next links in the pathway activated by the AT2 receptor, so as to use them to modify the protein according to the invention-AT2 receptor interaction.

The subject of the present invention is also a method for characterizing the domains involved in the ATIP protein-AT2 receptor interaction, characterized in that it comprises:

(a) cotransforming a suitable yeast strain with two vectors, as defined above, namely (i) a vector encoding a fragment containing at least SEQ ID NO:5 of the ATIP protein, mutated or not, fused with a protein selected from the group consisting of the DNA-binding domain of a transcription factor and the activation domain of the said transcription factor and (ii) a vector encoding a fragment containing the C-terminal end of the AT2 receptor, mutated or not, fused with a protein selected from the group consisting of the DNA-binding domain of a transcription factor and the activation domain of the said transcription factor, which vectors comprise, in addition, selectable markers, one of the two vectors necessarily encoding a mutated protein, and (b) visualizing, by selection on a suitable selective medium, the possible loss of the ATIP-AT2 receptor interaction.

Such a method makes it possible to identify and to delimit the important domains of the ATIP protein or of the C-terminal end of the AT2 receptor, on which their interaction depends, so as to use them as preferred target for modifying the AT2 receptor signalling.

The subject of the present invention is also a method for selecting substances capable of influencing the ATIP protein according to the invention-AT2 receptor interaction, which method comprises:

(a) bringing the ATIP protein, attached to a support, into contact with a fusion protein AT2 receptor-protein tag, optionally in the presence of a substance to be tested, (b) at least one washing of the said support thus treated with a suitable buffer, and (c) visualizing the possible ATIP-AT2 receptor interaction, in particular in SDS-PAGE, followed by immunoblotting with antibodies directed against the protein tag, fused with the AT2 receptor, or against the AT2 receptor.

If the substance to be tested inhibits the ATIP-AT2 receptor interaction, the visualization step is negative.

In accordance with the invention, ATIP is attached to the said support either covalently, or through affinity binding between an attachment substance fused with ATIP and the said support. For example, the said support consists of beads coupled either to a substance having affinity with the said attachment protein, fused with ATIP, or to suitable antibodies.

The fusion protein AT2 receptor-protein tag is in particular obtained from a lysate of cells transfected with a vector expressing the fusion protein AT2-protein tag.

As a variant, the said method for selecting substances capable of interacting with the ATIP protein according to the invention comprises:

(a) bringing the ATIP protein, attached to a support, into contact with a cell lysate, (b) at least one washing of the said support thus treated with a suitable buffer, (c) visualizing the possible protein combined with the ATIP protein, in particular in SDS-PAGE, followed by immunoblotting with appropriate antibodies, and (d) identifying the protein in the cell lysate interacting with the ATIP protein.

In accordance with the said method for selecting substances capable of influencing the ATIP protein according to the invention-AT2 receptor interaction, it is possible to use in particular, as fusion proteins ATIP-protein tag, the proteins GST-ATIPc and MYC-ATIPc, which constitute tools which can make it possible to bring down in vitro any proteins interacting with ATIP, for example, from cell lysates activated or otherwise with ligands for the AT2 receptor. The GST-ATIP protein may be brought down by specific interaction of GST with agarose beads coupled to glutathione, or alternatively immunoprecipitated with the anti-ATIP antibody. The Myc-ATIP protein may be immunoprecipitated with commercial anti-MYC antibodies or with the anti-ATIP antibody.

The advantage of these methods consists in finding means of modifying the signalling, the level of expression or the pharmacology of the AT2 receptor, which may have therapeutic applications. Indeed, when a pathological condition has been clearly correlated with a transduction abnormality associated with the AT2 receptor, modification of this transduction, in particular by acting on the binding of the AT2 receptor to the protein according to the invention, may then possibly compensate for the pathological disorder or at least influence it.

The subject of the present invention is also the use of the abovementioned cotransformed cells for the selection and screening of substances or of proteins capable of influencing the ATIP protein-AT2 receptor interaction or capable of interacting with the ATIP protein.

In addition to the preceding features, the invention also comprises other features which will emerge from the description which follows, which refers to exemplary embodiments of the method which is the subject of the present invention as well as to the accompanying drawings, in which:

FIG. 1 corresponds to the C-terminal end of the mouse AT2 receptor, used as a two-hybrid bait for screening a mouse cDNA library;

FIG. 3 illustrates the presumed coiled-coil structures (coiled-coil domains underlined) of mouse ATIP;

FIG. 4 illustrates the presumed coiled-coil structures (coiled-coil domains underlined) of human ATIP;

FIG. 6 illustrates the multiple cloning site of the plasmid pRSET A;

FIG. 8 illustrates the structure of the plasmid pBAC-PAK-poly HIS;

FIG. 11 illustrates the modifications of the signal induced by the AT2 receptor by overexpression of the ATIP protein.

It should be clearly understood, however, that these examples are given solely by way of illustration of the subject of the invention and do not constitute in any manner a limitation thereto.

EXAMPLE 1

Demonstration of a Specific Protein-protein Interaction between the AT2 Receptor and the Protein having the Sequence SEQ ID NO:6 According to the Invention Materials and Methods The two-hybrid system, initially developed by Song and Fields in 1989 (Nature, 340, 245–246) is based on the fact that the activity of numerous eukaryotic transcription-activating factors requires only two domains: an activating domain which does not have the capacity to bind DNA and a DNA-binding domain.

In the two-hybrid system, the DNA-binding domain is fused with a protein X and the activation domain is fused with a protein Y. If, and only if, X and Y interact, a complex is formed which reconstitutes a functional transcription factor.

Figure 2:
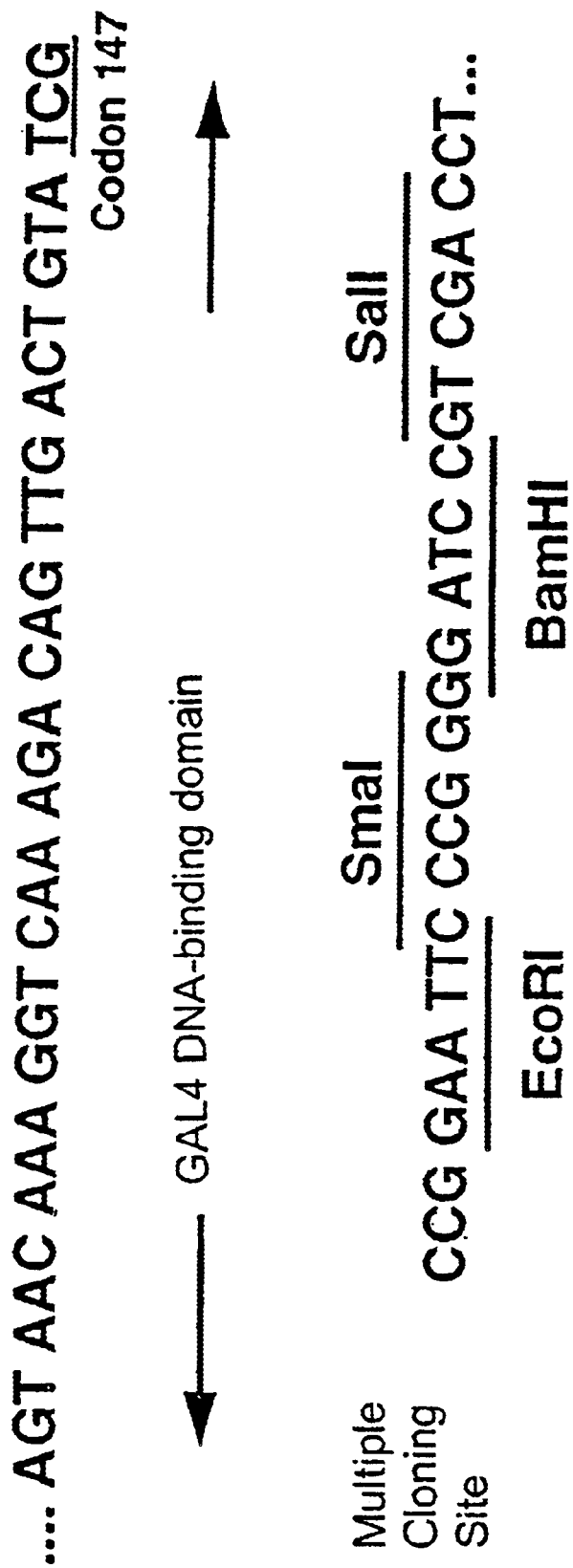
FIG. 2 illustrates the position of the GAL4-binding domain and the multiple cloning site of the plasmid pGBT9 (Clontech)

Construction of the expression vectors:

"bait" vectors:

Protein X: C-terminal end of the sequence encoding the mouse AT2 receptor (52 amino acids of CVNPF at the stop codon, see FIG. 1), fused with the sequence encoding the Gal4 DNA-binding domain (FIG. 2).

Insert: end of the mouse AT2 receptor (159 bp+16 bp of sites generated by PCR) inserted at the level of the EcoRI and BamHI sites of the vectors pLEX9 (Clontech) or pGBT9 (modified pGAD424 or pBTM116; A. B. Vojtek et al., Cell, 1993, 74, 205–214).

Figure 5:
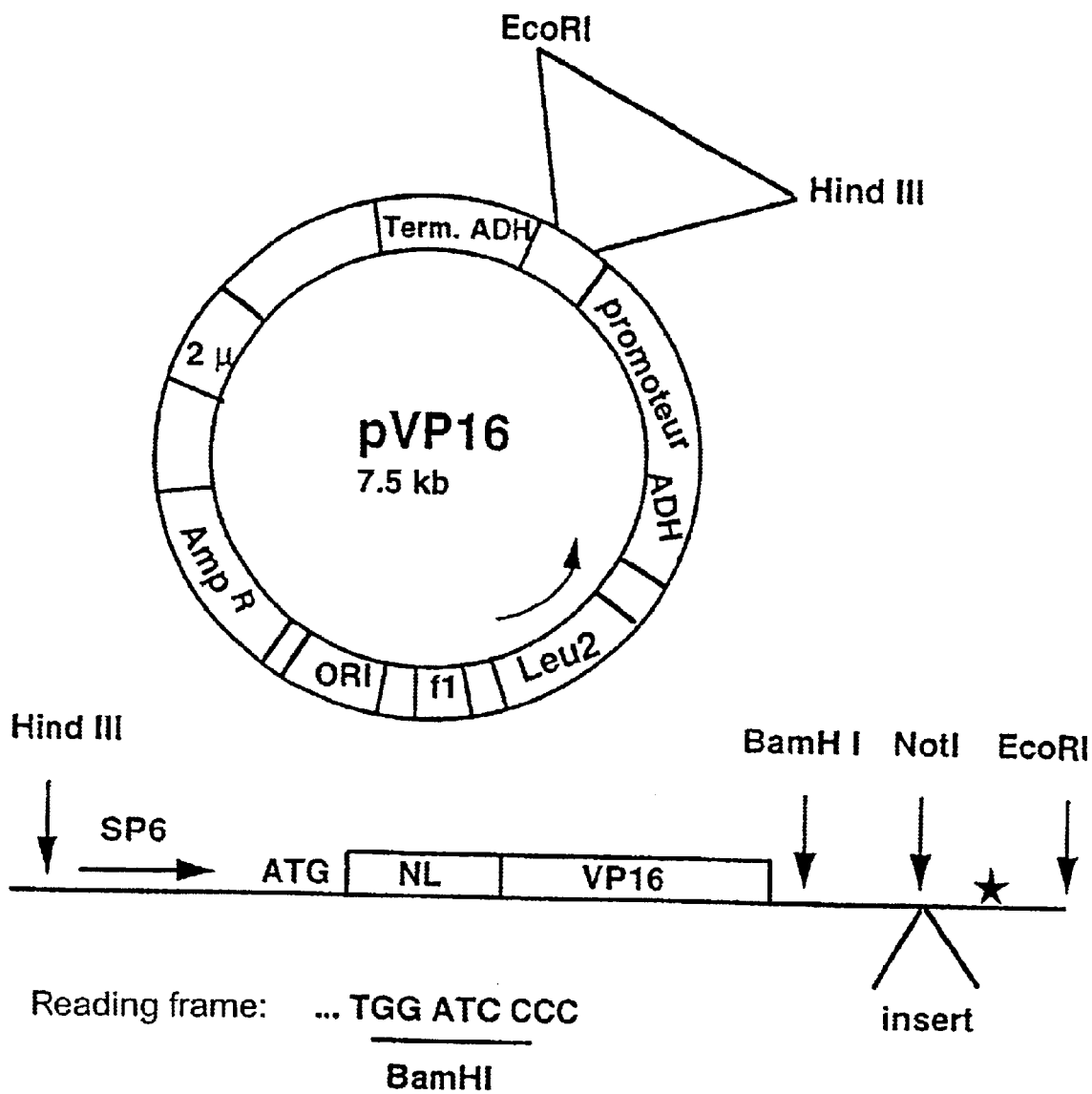
FIG. 5 illustrates the structure of the plasmid pVP16.

The following sequence is thus obtained: CGGAATTC on the 5' side-AT2 C-terminal sequence of 52 amino acids-GGATCCCG 3' side screened library:

mouse foetal cDNA library (A. B. Vojtek et al., *Cell*, 1993, 74, 205–214), containing inserts of 350 to 700 bp (protein Y) in the vector VP16 (FIG. 5).

"Bait" control vectors

Protein X: C-terminal end of the human β2-adrenergic receptors, rat AT1 or human bradykinin.

Transformed yeast strain

HF7c (Clontech) for the bait constructed in pGBT9;

L40 for the bait constructed in pLex9.

Results

This strategy made it possible to isolate a clone derived from the cDNA library containing an insert of 354 bp (ATIP) which interacts specifically with the C-terminal end of AT2. It is of interest to note that the screening of this library with the constructs produced in the two expression vectors pGBT9 and pLEX9 made it possible to find this same clone in both cases. This clone does not interact with control proteins exhibiting nonspecific interactions.

To evaluate the selectivity of this interaction, the ATIP clone was tested as a two-hybrid system with the C-terminal ends of the receptors: human β2 adrenergic, rat AT1 and human bradykinin, and all gave negative results. This indicates that the polypeptide encoded by the ATIP clone interacts, in a selective manner, with the C-terminal end of the mouse AT2 receptor.

EXAMPLE 2

Characterization of the ATIP Clone

To test for the corresponding whole clone, a probe of 354 bp (SEQ ID NO:5), which corresponds to the insert obtained by digestion with the restriction enzyme NotI of the plasmid isolated in a two-hybrid system (that extracted from the VP16 library, selected as being positive in the screen using, as bait, the C-terminal end of the mouse AT2 receptor), is used to screen a mouse foetal cDNA library constructed with inserts of more then 1 kb in size. Two overlapping clones, comprising the ATIP sequence, were thus identified and made it possible to sequence 1803 bp of the corresponding cDNA (SEQ ID NO:1). This sequence contains an open reading frame of 1323 bp (SEQ ID NO:3), potentially encoding a protein of 440 amino acids (SEQ ID NO:2 and 4). Comparisons between the identified protein sequence and the sequences contained in data banks indicate that it never exhibits more than 25% homology with a known sequence part.

The 354 bp probe (SEQ ID NO:5) was used as probe in Southern and Northern in a very satisfactory manner under the hybridization conditions below: prehybridization and hybridization in 45% formamide, 9% dextran sulphate, 0.2% BSA, 0.2% polyvinylpyrrolidone, 0.2% Ficoll, 0.1% sodium pyrophosphate, 0.01% SDS, 0.05 mM Tris pH 7.5, 0.9 M NaCl and rinses to stringency: 1×SSC, 0.1% SDS.

In parallel, Northern blot hybridization experiments carried out on total RNAs of N1E-115 cells with the ATIP probe (SEQ ID NO:5) confirm the expression of the corresponding mRNA in the N1E-115 cells, and indicates the existence of at least 5 transcripts of different sizes. These transcripts correspond to alternative splicings of the same gene or to different homologous genes.

On a Northern, performed under the conditions described in the literature on a 5 μg sample of poly A+ RNA of N1E-115 cells, the sizes of the various transcripts hybridizing with the ATIPmouse probe are=2.5–3.5–5–5.3 and 7.5 kb.

Figure 9:
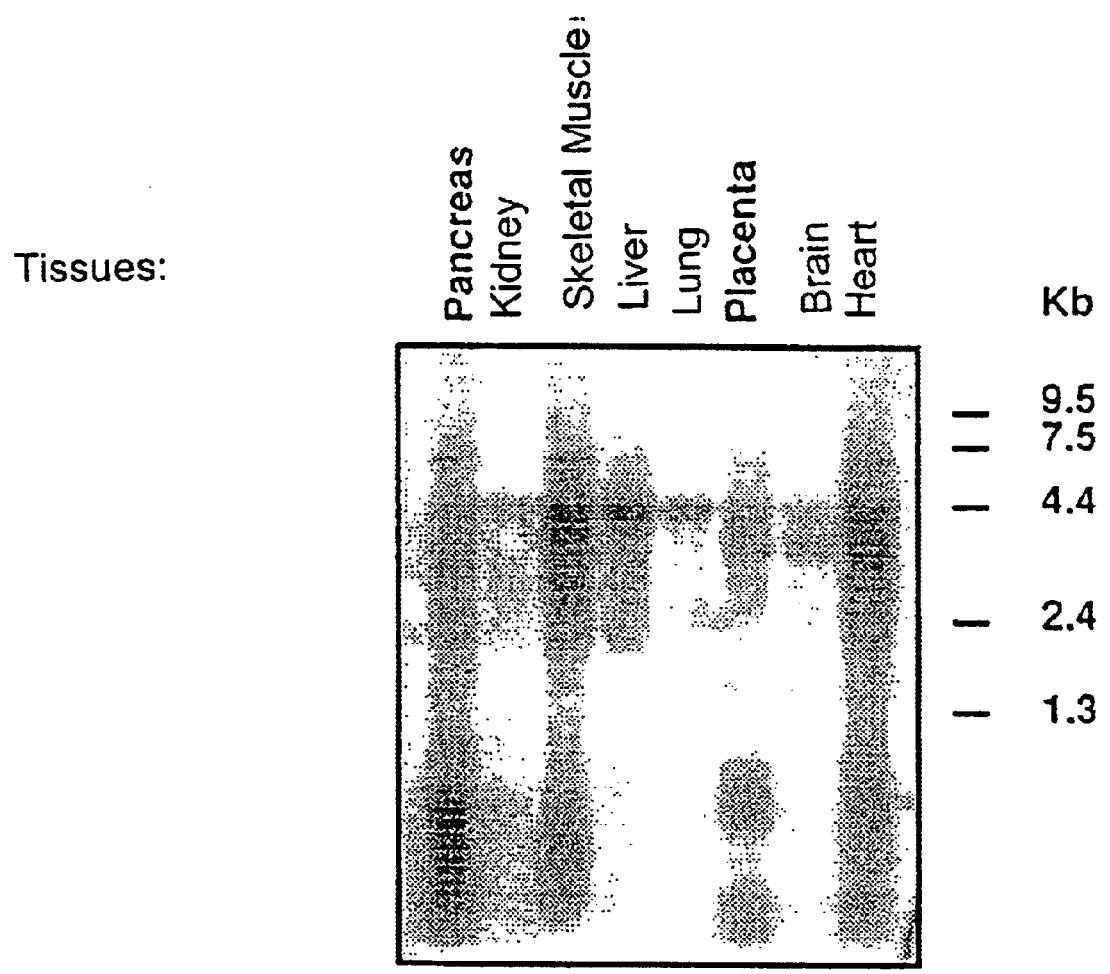
FIG. 9 illustrates a Northern blot of several human tissues hybridized with the probe ATIPmouse-short (SEQ ID NO:5)

FIG. 9 represents a Northern blot containing poly A+ RNAs of various human tissues, hybridized with the same ATIPmouse probe. It is possible to observe that ATIP is ubiquitously expressed. A predominant transcript at 4.4 kb is found in all the tissues represented, to which there are added, according to the tissues, other longer transcripts (pancreas and heart) or shorter transcripts (pancreas, skeletal muscle, placenta, brain and heart). These are perhaps the fruit of an alternative splicing of the ATIP RNA which would be dependent on the tissue considered or alternatively they are the sign of the existence of an RNA family encoding proteins of the "ATIP family" homologous to ATIP and which are revealed by the probe, at the stringency used.

To know the size of the smallest transcript encoding ATIP, a rapid amplification of the cDNA ends (5' RACE, Marathon cDNA Amplification Kit from Clontech) from poly A+ RNA of N1E-115 cells was carried out using the antisense oligonucleotide of SEQ ID NO:10, to amplify the 5' parts of the various mRNAs corresponding to the endogenous ATIP of the N1E-115 cells (murine neuroblastoma).

The results obtained indicated that the smallest transcript including the ATIP domain is an mRNA of 1950 bp, which indeed contains the start of the coding sequence obtained by cloning.

Any other pair of oligonucleotides (primers) of more than 20 bp and comprising part of the ATIP sequence may also be used to amplify, by PCR (PCR conditions to be determined for each pair of oligonucleotides with the aid of the OLIGO 4 software), part of the ATIP (and to give a DNA fragment which may be optionally used as a probe to recognize the DNA or the RNA corresponding to the ATIP).

EXAMPLE 3

Construction of Various Vectors According to the Invention

In general, the vectors containing ATIPmouse-short (with the exception of pRSETA-ATIPmouse-short) were obtained from an insert produced by PCR with the following two oligonucleotides (SEQ ID NO:11 and SEQ ID NO;12):

oligo. sense: 5' CGCGGATCCCAGACAGACCGGACGG AACTGGAG3' oligo. antisense: 5'CCGGAATTCACTACAACCTTTCGTT TAAAGCATC 3', using as template the vector VP16-ATIPmouse-short (FIG. 5). For the sake of convenience, this vector is called $^B$ATIPc$^{stop, E}$. Indeed, digested with BamHI and EcoRI, it gives an insert corresponding to the sequence

```
1st strand: GATCC-SEQ ID NO:5 (minus CAT)-TAGTG
2nd strand: CCTAG-------------------------CTTAAG
                                    (STOP)
   BamHI site                         EcoRIsite
```

Figure 7:
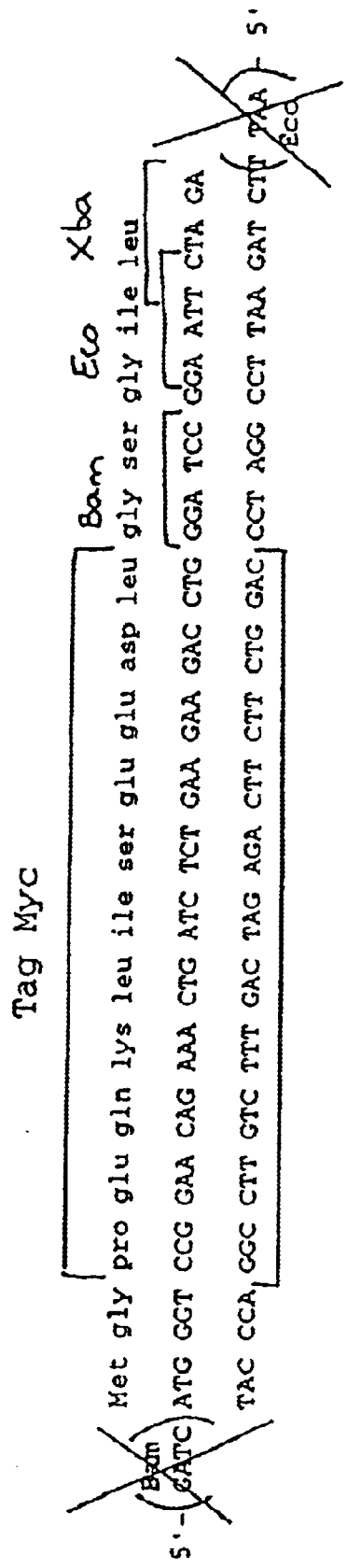
FIG. 7 illustrates the MCY sequence used to construct the plasmid pcDNA3-MYC.

Other vectors may also be constructed; they comprise all or part of the ATIP protein and are the following:

VP16-ATIPmouse-short (vector taken from the library screened in the two-hybrid system, comprises 354 bp (SEQ ID NO:5), inserted in NotI into VP16).

pCDNA3-MYC-ATIPmouse-short (insert $^B$ATIPc$^{stop, E}$, inserted in BamHI-EcoRI into pCDNA3-MYC (pcDNA3 from Invitrogen, modified by insertion of the MYC sequence, FIG. 7); this plasmid may be used in stable or transient transfections. It makes it possible to express MYC-ATIPmouse-short in eukaryotic cells. The expression of this protein in eukaryotic cells after transfection of the corresponding plasmid has already been obtained and checked by immunoreaction with an anti-MYC and anti-ATIP antibody.

pRSETA-HIS-ATIPmouse-short (insert $^B$ATIPc$^{stop, E}$, inserted in BamHI-EcoRI into pRSETA, Invitrogen). This plasmid makes it possible to express the fusion protein HIS-ATIPmouse-short in bacterial cells and to purify it on a nickel column (see FIG. 6 for the multiple cloning site).

pBacPAK-polyHIS-ATIPmouse-short (insert $^B$ATIPc$^{stop, E}$, inserted in BamHI-EcoRI into the vector pBacPAK-polyHIS (commercial pBacPAK, modified by insertion of a sequence containing a histidine tag and a site for cleavage with thrombin, FIG. 8). This construct may be used to express the ATIPmouse-short protein, fused with a histidine tag, in insect cells (SF9 type). Indeed, as indicated, this vector contains a polyhistidine insert and can therefore encode the fusion protein. The latter, like the fusion protein cloned into pRSET, may be purified on a nickel column and may serve in the same type of techniques.

pGEX-4T1-GST-ATIPmouse-short (insert amplified by the PCR identical to $^B$ATIPc$^{stop, E}$, but with no STOP codon, which extends the ATIPmouse-short sequence by the few amino acids which follow: Phe-Glu-Phe-Pro-Gly-Arg-Leu-Glu-Arg-Pro-His-Arg-Asp obtained from the plasmid pGEX-4T-1 (Pharmacia). This plasmid makes it possible to express the protein GST-ATIPmouse-short in bacterial cells and to purify it on glutathione-agarose beads.

pCDNAI-ATIPmouse clone1 (entire 5' sequenced from ATIP and ORF up to bp: 1205 starting from the beginning of the clone, inserted in BstxI into pCDNAI). This plasmid is derived from the cloning of the mouse foetal library with the probe SEQ ID NO:5. This plasmid can serve to produce, in bacteria, the 5' portion of the ATIPmouse DNA, so as to use it as a probe.

pCDNAI-ATIPmouse clone2 (2nd half of the ORF of ATIP from bp: 616 and up to the end of the 3' sequenced (bp 1803), inserted in BstxI into pCDNAI, Invitrogen). This plasmid can serve to produce, in bacteria, the 3' portion of the ATIPmouse DNA, so as to use it as a probe.

pCDNAI-ATIPmouse-long (clones 1 and 2 placed end to end, using the intermediate SapI site. This plasmid contains the entire ATIPmouse clone, inserted in BstxI into pCDNAI). This plasmid may be used in transient transfections in eukaryotic cells.

pCDNA3-ATIPmouse-long (whole ATIPmouse from BamHI-XbaI of pCDNAI-ATIPmouse-long, and inserted into pcDNA3, Invitrogen, at these same sites). This plasmid may be used in stable or transient transfections in eukaryotic cells. It made it possible to translate in vitro (kit TNT T7 coupled reticulocytes lysate systems, Promega) the whole ATIP protein and to observe that its translational product has an apparent molecular weight on gel of 58 kDa. Added to this predominant product are two minor products of 30 and 15 kDa. According to the ATIP sequence, these could correspond to partial products of translation in vitro starting with ATGs other than that at position 178 of SEQ ID NO:1.

EXAMPLE 4

Production of Stable Clones Expressing the ATIPmouse-short or Long Protein

Stable clones expressing both the human AT2 receptor and ATIPmouse-short (SEQ ID NO;6) or ATIPmouse-long (SEQ ID NO:3) were obtained by transfection.

CHO cells, deficient in dihydrofolate reductase, are transfected with a plasmid containing the region encoding the human AT2 receptor (Bedecs et al., *Biochem. J.* 1997, 325, 449–454).

The clone selected, CHO-hAT2, expressing 100 fmol of AT2 receptor/mg of protein, is cultured on an HAMF12 medium supplemented with 10% foetal calf serum and used between passages 10 and 30.

This clone was itself transfected with the plasmids pCDNA3-MYC-ATIPmouse-short or pCDNA3-ATIPmouse-long described in Example 3. The selection of the clones stably expressing the ATIP protein (short form or long form) was carried out in a selective medium containing 800 µg/ml of G418. The cell lysates, corresponding to the various selected clones, were subjected to SDS-PAGE followed by immunoblotting and this was incubated with the anti-ATIP polyclonal antibody. The results obtained indicate that various clones expressing various levels of ATIPmouse-short were able to be obtained.

EXAMPLE 5
Production of Polyclonal Antibodies Directed Against the SEQ ID NO:6 Sequence To progress in the characterization of this clone, the production of polyclonal antibodies directed against the ATIP domain was undertaken.

For that, a vector encoding a protein corresponding to this domain fused with six histidine residues was constructed.

The following sequence:

GGA TCC-SEQ NO:5-TAG-TGA-ATT is inserted into the plasmid pRSETA, as defined above.

In this insert, SEQ ID NO:5 does not comprise the first CAT.

The plasmid obtained is expressed in the *E. coli* strain BL 21 (DE3) (F$^-$ ompT$^-$ r$_B^-$ m$_B^-$) containing the bacteriophage DE3 which carries a DNA fragment containing the lacI gene, the lacUV5 promoter, the start of the lacZ gene and the gene encoding T7 RNA polymerase. This fragment is introduced into the int gene.

In the presence of DE3, only the lacUV5 promoter, inducible by IPTG directs the transcription of T7 RNA polymerase.

The addition of 0.4 mM IPTG to a culture of BL21 (DE3) cells induces the production of T7 RNA polymerase which, in turn, causes the transcription of the target DNA of the plasmid pRSETA (which allows the translation of the protein binding to the AT2 receptor).

The protein obtained (17 kDa) is purified on a nickel column (Ni-NTA, QuiAexpressionist 07/97, Quiagen), by virtue of the affinity of its six histidine residues for nickel. The protein obtained is then injected into rabbits so as to obtain polyclonal antibodies directed against the ATIP protein. The bleedings obtained have a very good titre.

These antibodies, purified on a GST-ATIP column, after passing through a GST column alone (so as to remove possible GST-specific antibodies and to retain on the GST-ATIP column only the antibodies specific for ATIPmouse-short) may be used successfully to immunoprecipitate and reveal in immunoblotting MYC-ATIPmouse-short from transiently transfected COS cells. Furthermore, this purified antibody also reveals in immunoblotting the ATIPmouse-long protein contained in lysates of COS cells transiently transfected with the plasmid pCDNA3-ATIPmouse-long.

The transfected ATIPmouse-long protein is visualized after SDS-PAGE and immunoblotting with an anti-ATIP antibody, in the form of two polypeptides having apparent molecular weights of 50 and 45 kDa.

This purified antibody was used in immunofluorescence on CHO-hAT2 cells, fixed by a 15-minute treatment with paraformaldehyde (3%). After fixing, the cells are successively treated with solutions of PBS/glycine 50 mM for 20 minutes, PBS/Tritonx100 0.1% for 5 minutes and PBS/BSA 0.2% for 15 minutes. They are then successively incubated in solutions containing 15 μg/ml of antibody containing the purified anti-ATIP antibody, and then the anti-rabbit immunoglobulin antibody coupled to rhodamine for 30 minutes. Between each new incubation, three rinses in PBS are carried out. Observations under a fluorescence microscope indicate an expression of the endogenous ATIP protein in the nucleus (predominantly) and in the cytoplasm of the CHO-hAT2 cells.

Some cells show a homogeneous distribution of the fluorescence due to the anti-ATIP antibody in these compartments, whereas other cells which appear more spread out, show a heterogeneous distribution of the fluorescence along the filaments which appear to start from the nucleus and spread up to the plasma membrane of the cell, in an organized network. Additional colocalization experiments should be carried out to determine if these filaments coincide or otherwise with known structures of the cytoskeleton.

EXAMPLE 6
Confirmation of the in Vitro Interaction of the ATIPmouse-short Protein with the C-terminal End of the AT2 Receptor To demonstrate the interaction of the ATIPmouse-short protein with the C-terminal end of the AT2 receptor in a system other than that of the two-hybrid system, a protocol which makes it possible to demonstrate this interaction in vitro was set up. For that, the fusion protein GST-ATIP as described above was produced; it is combined through its GST part with glutathione coupled to agarose beads (GA). In parallel, bacteria (DH5α) are transfected with a plasmid (pMAL-c2-AT2, derived from pMAL-c2 from New England Biolabs) encoding a fusion protein between the C-terminal end of the human AT2 receptor (Asn314-Ser363) and MBP (Maltose Binding Protein). These bacteria were cultured and the fusion protein was induced in 0.3 mM IPTG according to the protocol "pMAL Protein Fusion and Purification System" from New England Biolabs. After centrifugation of the culture at 4000 g and solubilization of the pellet obtained in "column buffer" (20 mM Tris-HCl, 200 mM NaCl, 1 mM EDTA), another centrifugation at 9000 g made it possible to recover a supernatant containing a high concentration of MBP-AT2. This supernatant was brought into contact, for 3 hours at 40° C., with glutathione agarose beads coupled to GST protein alone after addition of NaCl so as to have 300 mM final NaCl. This preincubation step makes it possible to remove the nonspecific interactions which may exist between ATIP and GA-GST. The supernatant recovered was brought into contact with the GA-GST-ATIPmouse-short or GA-GSTalone beads overnight at 4° C. After contact, the beads were rinsed three times in 20 mM Tris-HCl buffer, 300 mM NaCl, 1 mM EDTA and once in "column buffer". After analysing the beads rinsed in SDS-PAGE and immunoblotting with an anti-MBP antibody (New England Biolabs), a specific retention of the MBP-AT2 protein is observed on GA-GST-ATIPmouse-short beads which is not observed on the GA-GSTalone beads (FIG. 10).

Figure 10:
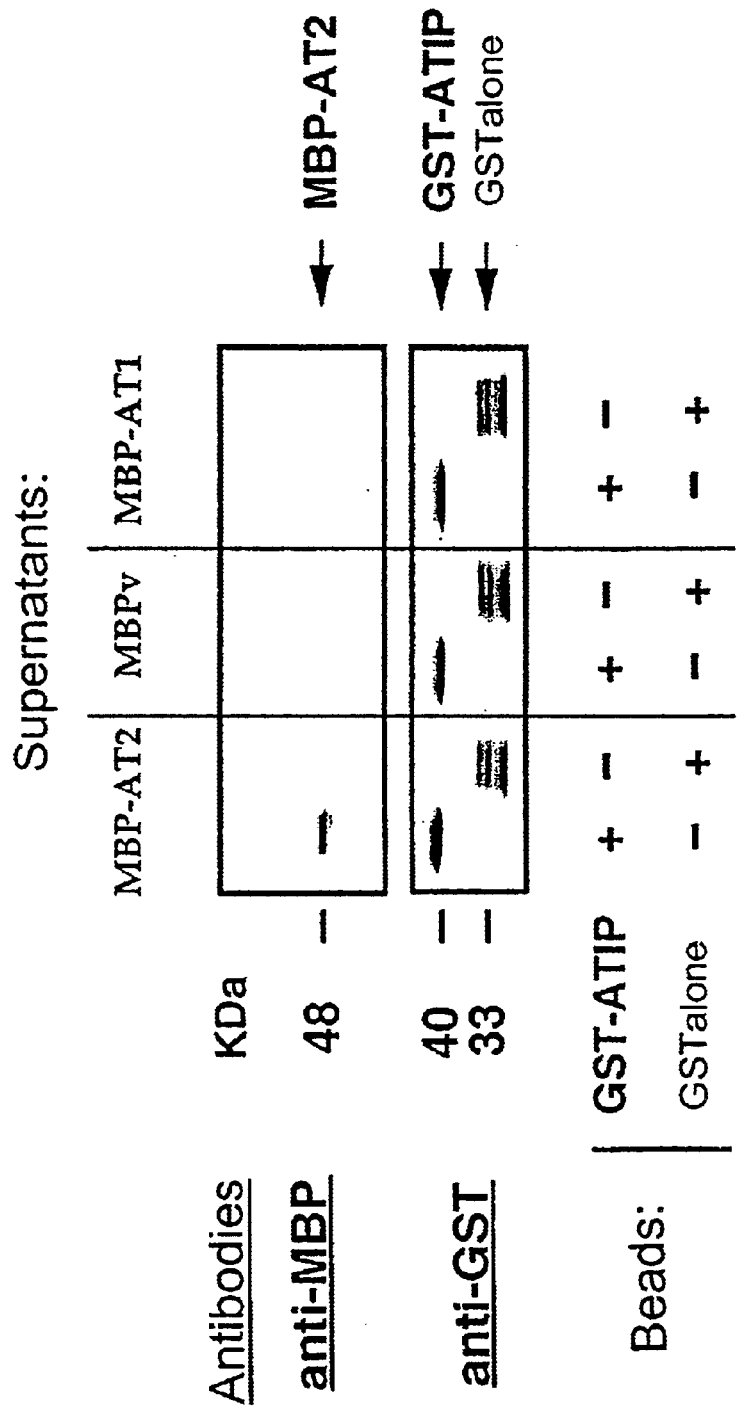
FIG. 10 illustrates the interaction in vitro of the protein ATIPmouse-short with the C-terminal end of the AT2 receptor.

This same protocol was carried out with a plasmid expressing MBP-AT1 (C-terminal end of human AT1 receptor (Leu 297-Glu 359)); it indicates that the MBP-AT1 protein is not retained in a specific manner on the GA-GST-ATIPmouse-short beads (FIG. 10).

These results confirm those obtained in the two-hybrid system indicating a specific and selective interaction between the protein according to the invention and the C-terminal end of the AT2 receptor (and not AT1).

EXAMPLE 7
Modification of the Transduction of the Signal for the AT2 Receptor in Clones Overexpressing the ATIPmouse-long Protein To verify that the ATIP protein interacts in vivo with the AT2 receptor, it was evaluated whether an overexpression of this protein modifies a signal induced by the AT2 receptor.

For that, a stable clone of CHO-hAT2 cells expressing the ATIPmouse-long protein (CHO-hAT2-ATIP), obtained according to the methodology described in Example 4, was used; the functional test for the activity of the AT2 receptor developed on the CHO-hAT2 clone which consists in inhibiting the phosphorylation of the IRβ subunit of the insulin receptor induced by its ligand, was reproduced.

Demonstration of an inhibition by the AT2 receptor of the phosphorylation of IRβ induced by insulin in CHO-hAT2 cells:

The CHO-hAT2 cells are inoculated at a density of 3×10[6] cells per dish having a diameter of 15 cm². They are made quiescent by 16 hours of deprivation before being treated. The treatment consists in bringing into contact for 5 minutes with 15 ml of F12 medium containing insulin supplemented or otherwise with CGP42112 (selective agonist of the AT2 receptor). After treatment, the cells are solubilized in lysis buffer containing: 50 mM Hepes, pH 7.6, 1% Triton X-100, 20 mM EDTA, 30 mM sodium pyrophosphate, 30 mM sodium fluoride, 2 mM benzamidine, 1 mM sodium orthovanadate, 1 mM phenylmethylsulphonyl fluoride and 1 µg/ml of aprotinin, pepstatin, antipain and leupeptin. The lysates are then subjected to purification on a wheatgerm lectin column, according to the protocol described in Issad, T. et al., (*Eur. J. Biochem.* 1995, 234, 108–115). After bringing into contact and washings, the lectin beads coupled to Sepharose (Pharmacia) are recovered in sample buffer containing SDS and the eluted proteins are analysed in SDS-PAGE followed by immunoblotting with anti-phosphotyrosine antibodies (Upstate Biotechnology, Inc.) or anti-IRβ antibodies (described in Issad, T. et al., cited above).

The β subunit of the insulin receptor appears as a polypeptide of 97 kDa whose phosphorylation (visualized by revealing with an anti-phosphotyrosine antibody) increases in a dose-dependent manner with the concentration of insulin. Angiotensin II (100 nM) as well as CGP42112 (100 nM) inhibit this phosphorylation at all the insulin doses tested between 0.1 and 0.001 µg/ml (FIG. 11). By way of example, CGP42112 inhibits the phosphorylation of IRβ induced by 0.01 µg/ml by a factor of 64±4% (n=7). This result demonstrates that the AT2 receptor interferes negatively with the signalling pathways for the insulin receptor at the initial stage of its activation, which is its autophosphorylation. These results also provide the first evidence of an interconnection between the signalling pathways for the tyrosine kinase receptors and the receptor with seven transmembrane domains which is AT2.

Reproduction of this methodology on CHO-hAT2-ATIP cells:

When this protocol is carried out on CHO-hAT2-ATIP cells, the inhibition by CGP42112 (100 nM) of the phosphorylation of the insulin receptor obtained for various doses of insulin (0.05, 0.01, 0.005, 0.001 µg/ml) is not observed (FIG. 11). This result was reproduced 3 times for each of the insulin doses taking, as positive control in each experiment, the inhibition obtained for the clone CHO-hAT2.

This therefore demonstrates that the overexpression of the ATIP protein in the CHO-hAT2 cells interferes with the AT2 receptor signalling, which confirms the interaction in vivo of the ATIP protein with the AT2 receptor.

Another glycosylated protein, retained on a lectin column, having an apparent weight of 120 kDa, identified as being the newly cloned protein SIRP (Kharitonenkov, A. et al., Nature, 1997, 386, 181–186) is phosphorylated on tyrosine in response to insulin. The phosphorylation of this protein, as well as that of IRβ is inhibited in the presence of CGP42112 in the case of the clone CHO-hAT2 and is not in the case of the clone CHO-hAT2-ATIP. This confirms that the ATIP protein interferes with the signalling pathways for the AT2 receptor. These results indeed show the possible value of the use of the ATIP protein for modifying signalling mediated by the AT2 receptor and for possibly compensating for pathological conditions associated with abnormalities in the regulation of this receptor.

As is evident from the above, the invention is not at all limited to those of its embodiments, implementations and applications which have just been described more explicitly; it encompasses, on the contrary, all the variants thereof which may occur to the specialist in the field, without departing from the framework or the scope of the present invention.

What is claimed is:

1. Isolated nucleic acid fragment, encoding a protein capable of binding to the AT2 receptor, which fragment is selected from the group consisting of the sequences SEQ ID NO:1, 3, 7 and 9.

2. Probe or primer, wherein it comprises from 20 to 400 bp of SEQ ID NO:1, 3, 5, 7 or 9, or to the complementary sequences of said sequences.

3. Fragment according to claim 2, characterized in that it is selected from the group consisting of the sequences SEQ ID NO:5, SEQ ID NO:10, SEQ ID NO:11 and SEQ ID NO:12.

4. Transcripts, characterized in that they are complementary to the sequences according to claim 1.

5. Recombinant, cloning and/or expression vector, characterized in that it comprises a nucleotide sequence according to claim 1 or sequence SEQ ID NO:5.

6. Transformed host cell, characterized in that it comprises a vector according to claim 5.

7. Transformed host cells, characterized in that they consist of a suitable yeast strain cotransformed with at least two vectors which respectively encode (i) a so-called bait protein selected from the group consisting of a fragment containing at least SEQ ID NO:5 encoding a fragment of the AT2 interacting protein, and a fragment encoding at least the C-terminal end of the AT2 receptor corresponding to cytoplasmic domain of said AT2 receptor, which bait protein is fused with a protein selected from the group consisting of the DNA-binding domain of a transcription factor and the activation domain of the same transcription factor and (ii) a so-called prey protein, selected from the group consisting of a fragment containing at least SEQ ID NO:5 encoding a fragment of the AT2 interacting protein, a fragment encoding at least said C-terminal end of the AT2 receptor and any other polypeptide corresponding to a sequence contained in a cDNA library, which prey protein is fused with a protein selected from the group consisting of the DNA-binding domain of a transcription factor and the activation domain of the same transcription factor, which vectors comprise, in addition, selectable markers.

8. Transformed host cell according to claim 7, characterized in that it consists of a suitable yeast strain cotransformed with three vectors which respectively encode (i) a bait corresponding to a fragment encoding the C-terminal end of the AT2 receptor corresponding to cytoplasmic domain of said AT2 receptor fused with a protein selected from the group consisting of the DNA-binding domain of a transcription factor and the activation domain of the said transcription factor, (ii) a fragment containing at least SEQ ID NO:5 encoding a fragment of the AT2 interacting protein, fused with a protein selected from the group consisting of the DNA-binding domain of a transcription factor and the activation domain of the said transcription factor and (iii) a polypeptide corresponding to a sequence contained in a cDNA library, which vectors comprise, in addition, selectable markers.

9. Transformed host cell according to claim 7, characterized in that it consists of a suitable yeast strain cotransformed with two vectors which respectively encode (i) a fragment containing at least the sequence SEQ ID NO:5 encoding a fragment of the AT2 interacting protein, fused with a protein selected from the group consisting of the DNA-binding domain of a transcription factor and the activation domain of the said transcription factor and (ii) a polypeptide corresponding to a sequence contained in a cDNA library, fused with a protein selected from the group consisting of the DNA-binding domain of a transcription factor and the activation domain of the said transcription factor, which vectors comprise, in addition, selectable markers.

10. Transformed host cell according to claim 7, characterized in that it consists of a suitable yeast strain cotransformed with two vectors, namely (i) a vector encoding a fragment containing at least the SEQ ID NO:5 encoding a fragment of the AT2 interacting protein, mutated or not, fused with a protein selected from the group consisting of the DNA-binding domain of a transcription factor and the activation domain of the said transcription factor and (ii) a vector encoding a fragment containing the C-terminal end of the AT2 receptor corresponding to positions 314–363 of said AT2 receptor, mutated or not, fused with a protein selected from the group consisting of the DNA-binding domain of a transcription factor and the activation domain of the said transcription factor, which vectors comprise, in addition, selectable markers, one of the two vectors necessarily encoding a mutated protein.

11. Method of detection of nucleic acid molecule encoding a protein of the ATIP family, comprising:

extracting total RNA from a biological sample, obtaining the corresponding cDNA, amplifying said cDNA with a pair of primers as defined in claim 2, hybridizing said amplified cDNA with a probe as defined in claim 2 under the following hybridization conditions: prehybridization and hybridization in 45% formamide, 9% dextran sulphate, 0.2% BSA, 0.2% polyvinylpyrrolidone, 0.2% Ficoll, 0.1% sodium pyrophosphate, 0.01% SDS, 0.05 mM Tris pH 7.5, 0.9 M NaCl and rinses to stringency: 1×SSC, 0.1% SDS.

* * * * *